(12) United States Patent
Furman et al.

(10) Patent No.: US 7,719,674 B2
(45) Date of Patent: *May 18, 2010

(54) IMAGE SPLITTING IN OPTICAL INSPECTION SYSTEMS

(75) Inventors: Dov Furman, Rehovot (IL); Shai Silberstein, Rishon-Le-Zion (IL); Effy Miklatzky, Jerusalem (IL); Daniel Mandelik, Rehovot (IL); Martin Abraham, Hod hasharon (IL)

(73) Assignee: Applied Materials South East Asia Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 11/944,677

(22) Filed: Nov. 26, 2007

(65) Prior Publication Data

US 2008/0137073 A1 Jun. 12, 2008

Related U.S. Application Data

(60) Provisional application No. 60/861,303, filed on Nov. 28, 2006.

(51) Int. Cl.
*G01N 21/00* (2006.01)
(52) U.S. Cl. ................................... 356/237.4
(58) Field of Classification Search .... 356/237.1–241.6
See application file for complete search history.

(56) References Cited

U.S. PATENT DOCUMENTS 2,045,093 A * 6/1936 Newcomer ................... 396/331

(Continued)

FOREIGN PATENT DOCUMENTS

EP 03 250 255 4/2006

(Continued)

OTHER PUBLICATIONS

Office Action dated Mar. 5, 2009, from U.S. Appl. No. 11/944,684 (filed Nov. 26, 2007), 16 pages.

(Continued)

*Primary Examiner*—Gregory J Toatley, Jr.
*Assistant Examiner*—Jarreas C Underwood
(74) *Attorney, Agent, or Firm*—Sonnenschein Nath & Rosenthal LLP

(57) ABSTRACT

In an optical inspection tool, an image of an object under inspection, such as a semiconductor wafer, may be obtained using imaging optics defining a focal plane. Light comprising the image can be detected using multiple detectors which each register a portion of the image. The image of the object at the focal plane can be split into two, three, or more parts by mirrors or other suitable reflecting elements positioned tangent to the focal plane and/or with at least some portion at the focal plane with additional portions past the focal plane so that the focal plane lies between the imaging optics and the splitting apparatus. In some embodiments, reflective planes may be arranged to direct different portions to different detectors. Some reflective planes may be separated by a gap so that some portions of the light are directed while some portions pass through the gap. Other splitting elements may comprise a group of transmissive and reflective areas interspersed in an element positioned at or in the focal plane, with some portions of the light are reflected to detectors while other portions pass through the element(s) to other detectors. Splitting apparatuses and elements may be cascaded.

16 Claims, 18 Drawing Sheets

U.S. PATENT DOCUMENTS

| | | | |
|---|---|---|---|
| 2,559,698 A * | 7/1951 | Bahre | 359/482 |
| 2,736,250 A * | 2/1956 | Papritz | 396/331 |
| 3,211,046 A | 10/1965 | Kennedy | |
| 3,598,467 A | 8/1971 | Pearson | |
| 3,652,167 A * | 3/1972 | Smith | 356/636 |
| 3,668,406 A * | 6/1972 | Reid et al. | 356/521 |
| 3,768,910 A | 10/1973 | Zanoni | |
| 4,011,403 A | 3/1977 | Epstein et al. | |
| 4,078,860 A * | 3/1978 | Globus et al. | 352/69 |
| 4,247,203 A | 1/1981 | Levy et al. | |
| 4,323,925 A * | 4/1982 | Abell et al. | 348/340 |
| 4,347,001 A | 8/1982 | Levy et al. | |
| 4,360,372 A | 11/1982 | Maciejko | |
| 4,378,159 A | 3/1983 | Galbraith | |
| 4,383,170 A * | 5/1983 | Takagi et al. | 250/216 |
| 4,456,339 A * | 6/1984 | Sommargren | 359/497 |
| 4,462,662 A | 7/1984 | Lama | |
| 4,486,776 A | 12/1984 | Yoshida | |
| 4,556,317 A | 12/1985 | Sandland et al. | |
| 4,556,791 A * | 12/1985 | Spillman, Jr. | 250/225 |
| 4,579,455 A | 4/1986 | Levy et al. | |
| 4,589,030 A * | 5/1986 | Kley | 348/367 |
| 4,589,736 A | 5/1986 | Harrigan et al. | |
| 4,597,665 A | 7/1986 | Galbraith et al. | |
| 4,601,576 A | 7/1986 | Galbraith | |
| 4,618,938 A | 10/1986 | Sandland et al. | |
| 4,639,587 A | 1/1987 | Chadwick et al. | |
| 4,644,172 A | 2/1987 | Sandland et al. | |
| 4,734,923 A | 3/1988 | Frankel et al. | |
| 4,760,265 A | 7/1988 | Yoshida et al. | |
| 4,766,324 A | 8/1988 | Saadat et al. | |
| 4,806,774 A | 2/1989 | Lin et al. | |
| 4,845,558 A | 7/1989 | Tsai et al. | |
| 4,877,326 A | 10/1989 | Chadwick et al. | |
| 4,898,471 A | 2/1990 | Stonestrom et al. | |
| 4,967,095 A | 10/1990 | Berger et al. | |
| 4,969,198 A | 11/1990 | Batchelder et al. | |
| 5,008,743 A | 4/1991 | Katzir et al. | |
| 5,016,109 A * | 5/1991 | Gaylord | 348/218.1 |
| 5,029,975 A | 7/1991 | Pease | |
| 5,056,765 A | 10/1991 | Brandstater | |
| 5,058,982 A | 10/1991 | Katzir | |
| 5,076,692 A | 12/1991 | Neukermans et al. | |
| 5,112,129 A | 5/1992 | Davidson et al. | |
| 5,153,668 A | 10/1992 | Katzir et al. | |
| 5,161,238 A * | 11/1992 | Mehmke | 359/738 |
| 5,194,959 A * | 3/1993 | Kaneko et al. | 348/335 |
| 5,264,912 A | 11/1993 | Vaught et al. | |
| 5,267,017 A | 11/1993 | Uritsky et al. | |
| 5,352,886 A * | 10/1994 | Kane | 250/216 |
| 5,381,004 A | 1/1995 | Uritsky et al. | |
| 5,381,439 A * | 1/1995 | English et al. | 372/108 |
| 5,386,228 A | 1/1995 | Okino | |
| 5,422,724 A | 6/1995 | Kinney et al. | |
| 5,519,675 A * | 5/1996 | Toofan | 369/13.29 |
| 5,537,168 A * | 7/1996 | Kitagishi et al. | 353/101 |
| 5,537,669 A | 7/1996 | Evans et al. | |
| 5,586,058 A | 12/1996 | Aloni et al. | |
| 5,604,585 A | 2/1997 | Johnson et al. | |
| 5,608,155 A | 3/1997 | Ye et al. | |
| 5,617,203 A | 4/1997 | Kobayashi et al. | |
| 5,619,429 A | 4/1997 | Aloni et al. | |
| 5,619,588 A | 4/1997 | Yolles et al. | |
| 5,659,172 A | 8/1997 | Wagner et al. | |
| 5,687,152 A | 11/1997 | Takeda et al. | |
| 5,699,447 A | 12/1997 | Alumot et al. | |
| 5,774,444 A * | 6/1998 | Shimano et al. | 369/110.02 |
| 5,797,317 A | 8/1998 | Lahat et al. | |
| 5,798,829 A | 8/1998 | Vaez-Iravani | |
| 5,822,055 A | 10/1998 | Tsai et al. | |
| 5,825,482 A | 10/1998 | Nikoonahad et al. | |
| 5,835,278 A * | 11/1998 | Rubin et al. | 359/636 |
| 5,864,394 A | 1/1999 | Jordan, III et al. | |
| 5,883,710 A | 3/1999 | Nikoonahad et al. | |
| 5,892,579 A | 4/1999 | Elyasaf et al. | |
| 5,907,628 A | 5/1999 | Yolles et al. | |
| 5,912,735 A | 6/1999 | Xu | |
| 5,917,588 A | 6/1999 | Addiego | |
| 5,939,647 A | 8/1999 | Chinn et al. | |
| 5,970,168 A | 10/1999 | Montesanto et al. | |
| 5,982,921 A | 11/1999 | Alumot et al. | |
| 5,991,699 A | 11/1999 | Kulkarni et al. | |
| 6,020,957 A | 2/2000 | Rosengaus et al. | |
| 6,021,214 A | 2/2000 | Evans et al. | |
| 6,064,517 A | 5/2000 | Chuang et al. | |
| 6,075,375 A | 6/2000 | Burkhart et al. | |
| 6,078,386 A | 6/2000 | Tsai et al. | |
| 6,099,596 A | 8/2000 | Li et al. | |
| 6,100,976 A * | 8/2000 | Ackerson | 356/336 |
| 6,122,046 A | 9/2000 | Almogy | |
| 6,124,924 A | 9/2000 | Feldman et al. | |
| 6,137,535 A * | 10/2000 | Meyers | 348/340 |
| 6,169,282 B1 | 1/2001 | Maeda et al. | |
| 6,172,349 B1 | 1/2001 | Katz et al. | |
| 6,175,645 B1 | 1/2001 | Elyasaf et al. | |
| 6,175,646 B1 | 1/2001 | Schemmel et al. | |
| 6,178,257 B1 | 1/2001 | Alumot et al. | |
| 6,208,411 B1 | 3/2001 | Vaez-Iravani | |
| 6,208,750 B1 | 3/2001 | Tsada | |
| 6,215,551 B1 | 4/2001 | Nikoonahad et al. | |
| 6,236,454 B1 | 5/2001 | Almogy | |
| 6,246,822 B1 | 6/2001 | Kim et al. | |
| 6,256,093 B1 | 7/2001 | Ravid et al. | |
| 6,267,005 B1 | 7/2001 | Samsavar et al. | |
| 6,268,093 B1 | 7/2001 | Kenan et al. | |
| 6,268,916 B1 | 7/2001 | Lee et al. | |
| 6,271,916 B1 | 8/2001 | Marxer et al. | |
| 6,274,878 B1 | 8/2001 | Li et al. | |
| 6,288,780 B1 | 9/2001 | Fairley et al. | |
| 6,317,514 B1 | 11/2001 | Reinhorn et al. | |
| 6,324,298 B1 | 11/2001 | O'Dell et al. | |
| 6,347,173 B1 | 2/2002 | Suganuma et al. | |
| 6,360,005 B1 | 3/2002 | Aloni et al. | |
| 6,361,910 B1 | 3/2002 | Sarig et al. | |
| 6,366,315 B1 | 4/2002 | Drescher | |
| 6,369,888 B1 | 4/2002 | Karpol et al. | |
| 6,456,769 B1 | 9/2002 | Furusawa et al. | |
| 6,542,304 B2 * | 4/2003 | Tacklind et al. | 359/618 |
| 6,628,681 B2 | 9/2003 | Kubota et al. | |
| 6,633,375 B1 | 10/2003 | Veith et al. | |
| 6,819,490 B2 | 11/2004 | Sandstrom et al. | |
| 6,892,013 B2 | 5/2005 | Furman et al. | |
| 6,895,149 B1 | 5/2005 | Jacob et al. | |
| 7,190,519 B1 * | 3/2007 | Kitagishi | 359/485 |
| 7,218,389 B2 | 5/2007 | Uto et al. | |
| 2001/0033386 A1 | 10/2001 | Kranz et al. | |
| 2002/0037099 A1 | 3/2002 | Ogawa et al. | |
| 2002/1006747 | 6/2002 | Karpol et al. | |
| 2003/0227618 A1 | 12/2003 | Some | |
| 2004/0032581 A1* | 2/2004 | Nikoonahad et al. | 356/237.2 |
| 2004/0146295 A1* | 7/2004 | Furman et al. | 398/9 |
| 2005/0084766 A1 | 4/2005 | Sandstrom | |
| 2008/0037933 A1 | 2/2008 | Furman et al. | |

FOREIGN PATENT DOCUMENTS

| | | |
|---|---|---|
| JP | 61262607 | 11/1986 |
| WO | WO 00/70332 | 11/2000 |

OTHER PUBLICATIONS

Response to Office Action filed Aug. 5, 2009, from U.S. Appl. No. 11/944,684 (filed Nov. 26, 2007), 10 pages.

Office Action dated Jul. 23, 2004, from U.S. Appl. No. 10/345,096 (filed Jan. 15, 2003), 13 pages.

Office Action dated Oct. 20, 2005, from U.S. Appl. No. 11/021,393 (filed Dec. 23, 2004), 18 pages.

Office Action dated Mar. 8, 2006, from U.S. Appl. No. 11/096,873 (filed Apr. 1, 2005), 8 pages.

Office Action dated Apr. 6, 2006, from U.S. Appl. No. 11/096,873 (filed Apr. 1, 2005), 8 pages.

Patent Abstracts of Japan, vol. 17, No, 613, Jul. 1993 & JP 05 190421.

Patent Abstracts of Japan, vol. 1996, No. 10, Jun. 1996 & JP 08 154210.

Patent Abstracts of Japan, vol, 1999, No. 04, Jan. 1999 & JP 11 014357.

Patent Abstracts of Japan, vol. 1997, No. 03, Nov. 1996 & JP 08 292361.

T.S. McKecknie, Speckle Reduction, pp, 123-170 in Topics in Applied Physics, vol. 9, Laser Speckle and Related Phenomena, edited by J.C. Dainty, Springer Verlag.

D. Kohler et al, Speckle Reduction in Pulsed-Laser Photography, published in Optics Communications, vol. 12, No. 1, pp. 24-28, Sep. 1974.

Dingel et al., Speckle Reduction with Virtual Incoherent Laser Illumination Using Modified Fiber Array, published in Optik, vol. 94, No. 3, pp. 132-136, 1993.

Dom, Byron et al., Machine Vision and Applications, 1998, 1:205-221.

Negevtech, EP 03250255, EP Search Report, Apr. 22, 2003, 5 pp.

U.S. Provisional Patent Application No. 60/415,082 filed Sep. 30, 2002.

* cited by examiner

IMAGE SPLITTING IN OPTICAL INSPECTION SYSTEMS

PRIORITY CLAIM

This application claims priority to U.S. Provisional Patent Application No. 60/861,303, filed Nov. 28, 2006 and entitled IMAGE SPLITTING IN OPTICAL INSPECTION SYSTEMS, which is hereby incorporated by reference herein in its entirety.

BACKGROUND

In wafer inspection systems which utilize two dimensional imaging, the inspection speed is determined, among other things, from parameters including field of view size, and time between imaging sequential images. Generally speaking, a larger field of view, or a shorter time between sequential images will increase the inspection speed.

Decreasing the time between imaging may be complicated and expensive. For instance, decreasing the time between images can require very fast detectors (much faster above normal 30 Hz detectors), fast illumination (for example, repetitive laser with hundreds of pulses per second), and a fast stage or other suitable components for generating relative motion between the wafer and imaging components to change which portion(s) of the wafer are in view for imaging.

A more preferable approach in some circumstances is to enlarge the field of view. However, when fine resolution is required (pixel size in the wafer plane is below 0.5 microns), the detector must contain a numerous pixels. For example, using 0.2 micron pixel, and a conventional commercial detector with 2K×2 K pixels, the field of view is only 0.4 mm×0.4 mm. An enlarged field of view may also require a faster stage or other suitable components for providing relative motion between the imaging components and the wafer.

The image view can be increased by using multiple two dimensional detectors to obtain an image, with the image divided amongst the detectors. Some currently-existing systems split an image before the focal plane of the other optics used to obtain the image using, for instance, beam splitters and/or mirrors. See, for instance, U.S. patent application Ser. No. 10/345,097, filed Jan. 15, 2003, and published as U.S. Patent Application Publication No., 20040146295 which are each incorporated by reference in their entireties herein. However, splitting an image by a mirror or other element(s) before the focal plane may be problematic in some instances. The problems may include, for example, reductions in intensity and/or non-uniform intensity.

FIG. 17 illustrates an example wherein the intensity in some parts of a split image is reduced when some rays are reflected back from the mirror and do not actually reach the focal plane, since the actual splitting of the image occurs prior to the focal plane. As shown in FIG. 17, three rays (R1, R2 and R3) from the imaging optics 18 of an inspection system reach point A in the focal plane $FP_{18}$ of the imaging optics if no splitting mirror is used (i.e., if the mirror shown in FIG. 17 is disregarded, all three rays reach point A). However, when the splitting mirror comprising reflective planes 902 and 904 is used, only two rays (R2 and R3) reach the detectors 908-1 and 908-2 in the split focal plane. The top ray (R1) is reflected back from the mirror.

FIG. 17 also illustrates an example of non uniform intensity that may result from splitting. The intensity reduction is position dependent—a given portion of the image that is closer to the splitting point will have a reduced intensity relative to a portion of the image far from the splitting point. In FIG. 17, point B' gets only about half of the rays (i.e. rays generally emanating from the bottom half part of the imaging optics), while point A', for example, gets more (about two thirds: from ray R2 to R3).

An example hypothetical intensity distribution in detector 908-1 and 908-2 imaging a uniform input image (1 and 11) is shown in FIG. 18. The image is darker at points closer to the splitting point, with denser cross-hatching representing progressively darker portions of the image (becoming darker from left to right in 908-2 and right to left in 908-1).

The angular distribution of the image is not preserved when an image is split in this manner. For a wafer inspection system, the angular distribution of the scattered or reflected light from the wafer contains information regarding the wafer characteristics. Using splitting mirrors before the focal plane changes the angular distribution since it blocks a range of ray angles and thus may result in reduced inspection accuracy.

When splitting by beam splitters, some of the rays (usually 50%) are reflected from the beam splitter while the rest of the rays are transmitted. This way does not break the uniformity or the angular distribution, but the intensity is reduced by 50%. When using more than one splitter to split an image into more than two portions, the intensity can be reduced even more.

SUMMARY

In embodiments of the present subject matter, an image can be split into two, three, or more parts by mirrors or other suitable reflecting elements. The elements may be positioned tangent to the focal plane of an inspection tool's imaging apparatus, may intersect with the focal plane, or may be positioned past the focal plane. Since not all of the splitting is performed before the focal plane of the imaging optics, disadvantages such as intensity reduction, reduction of angular distribution uniformity, reduction of intensity uniformity, and the like can be reduced or avoided. Generally, using one or more embodiments of the present subject matter, the image intensity may be more uniform, less reduced, and the angular distribution may remains relatively unchanged as compared to other approaches.

The image splitting components are placed within a wafer or other inspection tool comprising one or more imaging components that obtain an image of an object at a focal plane. Although several examples herein discuss wafer inspection, the presently-disclosed technology may be used for inspection of any kind of object(s) including, but not limited to, reticles, photomasks, flat panel displays, printed circuit boards, etc. Furthermore, the image splitting components and other presently-disclosed teachings may be used in conjunction with inspection tools other than the tool described in 10/345,097.

An inspection system can include at least two two-dimensional detectors, where the image at the focal plane is split between at least some of the detectors using at least one splitting apparatus and at least one point of the at least one splitting apparatus is placed within the focal plane. "Within the focal plane" can include placing one or more points of the apparatus at or tangent to the focal plane. In different embodiments, more or less of the splitting apparatus may extend before or past the focal plane, but at least some light comprising one or more parts of the image reaches the spatial location of the focal plane.

For example, the splitting apparatus can comprise two adjacent reflective planes defining an angle, with the image being split into two or more parts by using the reflective planes which direct at least one portion to a two-dimensional detector. In some embodiments, each reflective plane directs a respective portion of the image to a different detector. In other embodiments, the planes define a gap which allows at least one portion to pass through the gap to be focused on a two-dimensional detector. The portion(s) that do not pass through the gap can be directed by a respective reflective plane toward a different two-dimensional detector. In some embodiments, one or more edges of the reflective planes that define the sides of the gap at the focal plane may have an acute angle. This may reduce or avoid interference from the reflective plane(s) with the portion or portions that pass through the gap.

In some embodiments, the splitting apparatus can comprise a fan-like structure comprising a plurality of reflective planes. Each reflective plane can be positioned with at least one end of the reflective plane at the focal plane so that each reflective plane defines a fan angle with the focal plane. The planes may be reflective on both sides and oriented so that one or more potions of the image at the focal plane are directed from the front of one plane, to the back of another, and then towards one or more detectors. Light may be directed between two plates multiple times before being directed towards a detector. In some embodiments, the planes may be arranged so that the respective fan angles monotonically decrease for respective elements along a length of the focal plane in one direction, while the angles increase for the elements along the length of the focal plane in a direction opposite the first direction. In some embodiments, the fan-like structure may be asymmetrical, while in other embodiments, the structure is symmetrical across a center line of the focal plane of the imaging apparatus.

In some embodiments, the splitting apparatus can comprise an optical element positioned at an angle to the path of incidence of the light comprising the image of the object. The optical element can comprise a plurality of transmissive areas and a plurality of reflective areas. For instance, the different areas may be arranged in a checkerboard pattern. Detectors can be positioned to receive light from the respective transmissive and reflective areas.

The reflective planes may comprise any suitable shape or material. For instance, the plane(s) may comprise flat, angular, or curved portions. In some embodiments, a plane can be curved so as to focus the image at the focal plane to another focal plane or to a detector. Further, in some embodiments, the splitting apparatus can comprise multiple splitting apparatus of the same or different types. For example, a splitting apparatus can comprise a pair of reflective planes with a gap and a plurality of curved planes. As another example, multiple fan-like structures may be used.

By reducing or avoiding the effects associated with splitting images before the focal plane of a tool's imaging optics, advantageous results can be achieved. For example, the intensity and uniformity of the intensity of light comprising each portion of a split image can be substantially unaffected by the split, even if the image is split into at least three or at least four detectors. Similarly, in some embodiments, the image intensity and the angular distribution of light impinging on the two-dimensional detectors comprising an inspection system can be substantially unaffected by the split.

BRIEF DESCRIPTION OF THE DRAWINGS

A full and enabling disclosure including the best mode of practicing the appended claims and directed to one of ordinary skill in the art is set forth more particularly in the remainder of the specification. The specification makes reference to the appended figures, in which:

DETAILED DESCRIPTION

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the instant disclosure includes modifications and variations as come within the scope of the appended claims and their equivalents.

Figure 15:
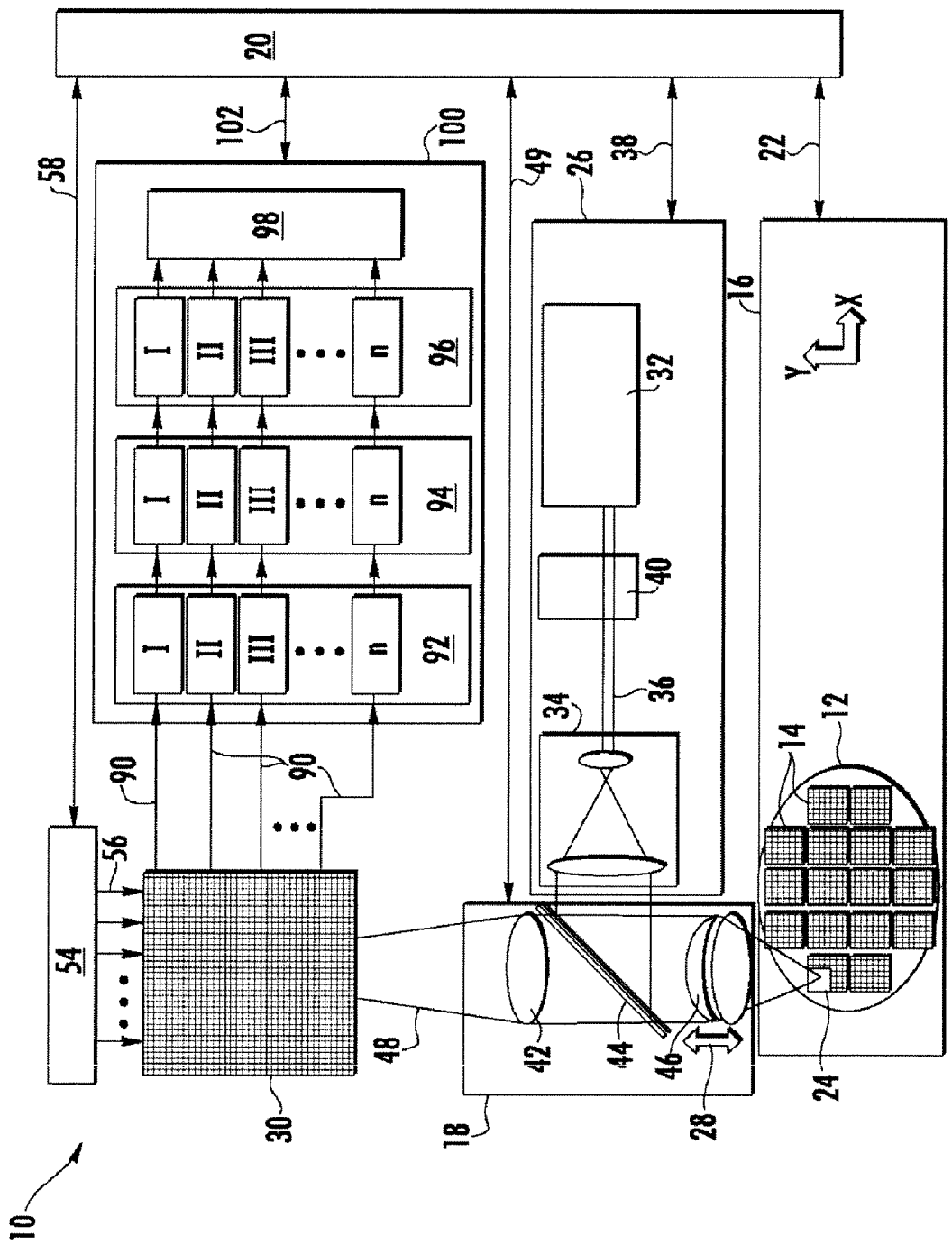
FIG. 15 is a block diagram showing illumination, imaging, and control components in an exemplary optical inspection tool.
Figure 16:
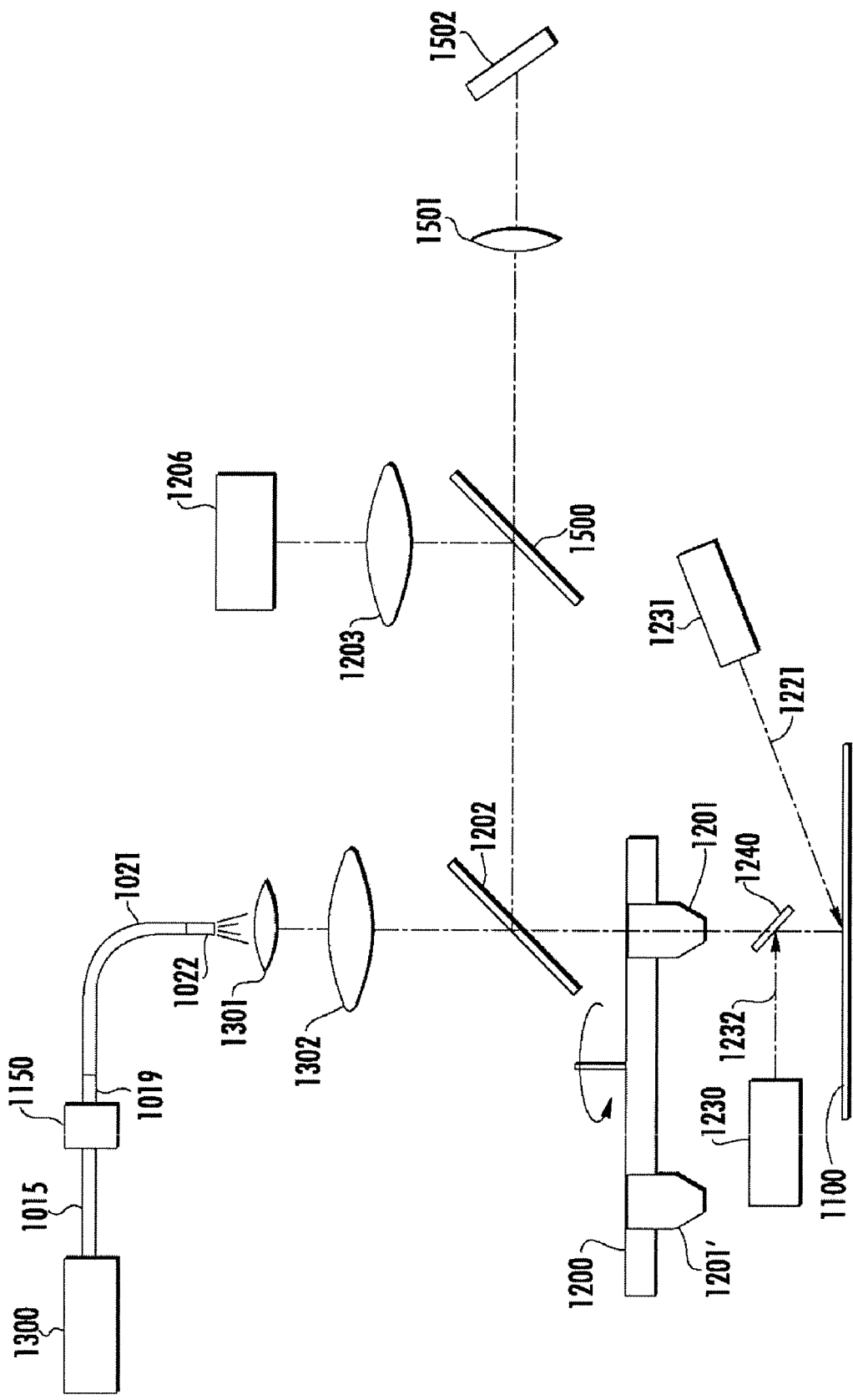
FIG. 16 is a block diagram showing additional aspects of imaging and illumination in an exemplary optical inspection tool.
Figure 17:
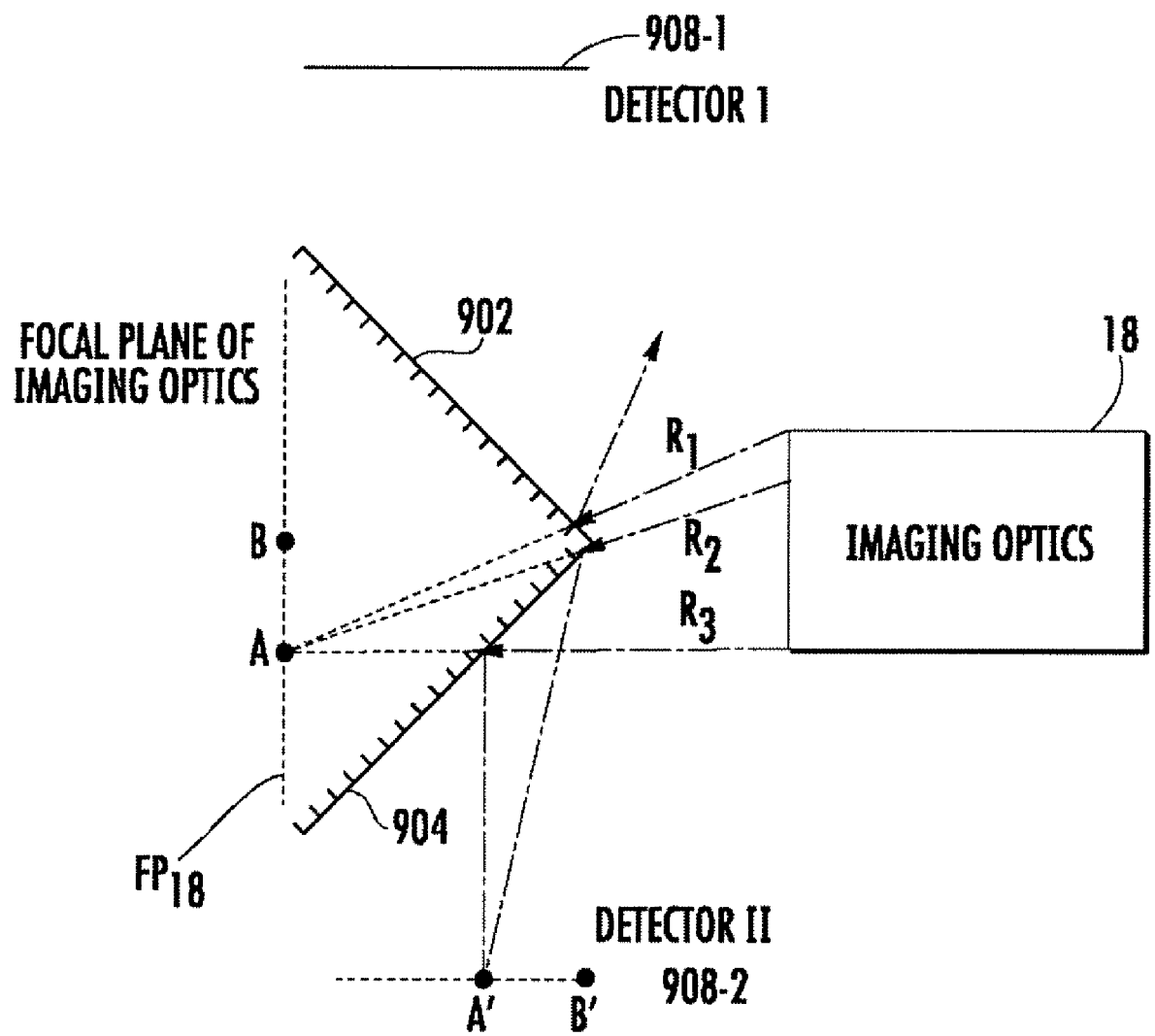
FIG. 17 is an illustration depicting an example where all splitting occurs before the focal plane of a set of imaging optics.
Figure 18:
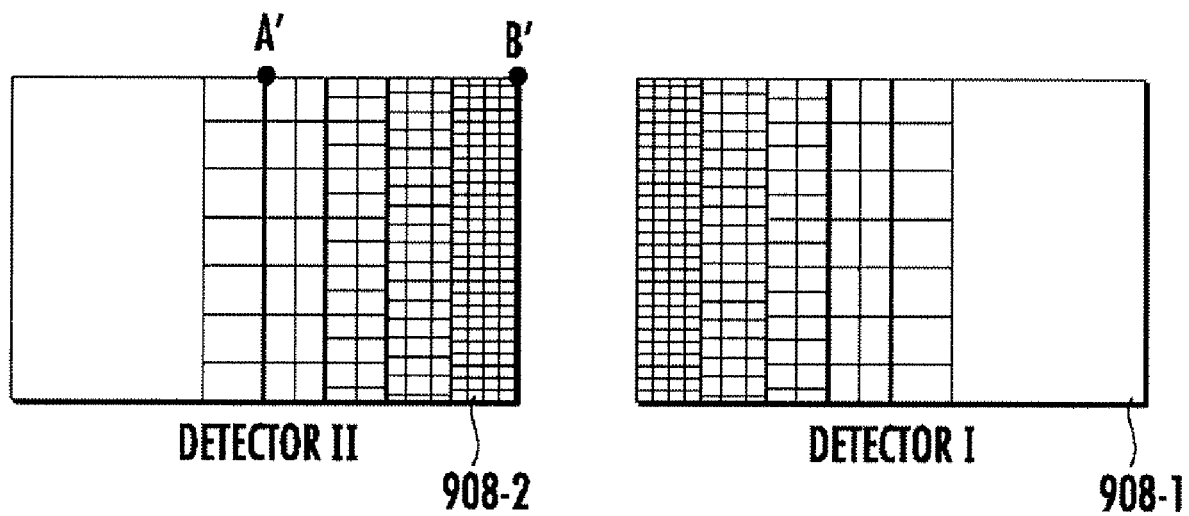
FIG. 18 is an illustration of exemplary hypothetical detector non-uniformities which may be introduced when all splitting occurs before the focal plane Use of like reference numerals in different features is intended to illustrate like or analogous components.

Before discussing exemplary embodiments of splitting apparatuses, FIGS. 15 and 16 will be discussed to place the splitting apparatus in context. In this example, FIG. 15 is a schematic diagram illustrating an exemplary embodiment of a system for fast on-line electro-optical detection of wafer defects, while FIG. 16 shows a schematic illustration of an object inspection system utilizing a laser source and a fiber optical delivery bundle in an exemplary inspection tool. For instance, the tool may comprise a Negevtech 3200 optical inspection tool (available from Negevtech, Ltd. of Rehovot, Israel), modified to use one or more embodiments of the presently disclosed splitting apparatus and methodologies. Additional details regarding exemplary aspects of an optical inspection system can be found in U.S. patent application Ser. No. 10/345,097. However, it is to be noted that the image splitting principles discussed below can be used in any suitable inspection system that creates an image of an object at a focal plane.

As shown in FIG. 15, an inspection tool can include a focal plane assembly 30 comprising pixels from multiple two-dimensional detectors. Focal plane assembly 30 is configured so that a continuous surface of photodetectors is optically formed at the focal plane of imaging optics 18. The actual photodetectors can be located at different geometric locations. In embodiments of the present subject matter, the inspection image obtained at the focal plane of imaging optics 18 can be split using one or more embodiments of a splitting apparatus as discussed in the examples below.

In operation, the dies 14 of wafer 12 can be illuminated in any suitable manner, such as by laser light from pulsed illumination system 26. Light 48 represents rays of light scattered, reflected, and diffracted by the wafer. This light can be collected using imaging optics 18. In this example, imaging optics 18 comprise a beam splitter 44 (used in illuminating wafer 12 with light from laser system 26), focusing lens 42, and an objective lens 46 which may be adjusted using an auto-focus system 28 (not shown in detail). In this example, focusing lens 42 focuses light 48 onto focal plane assembly 30 and defines the focal plane of imaging optics 18, referred to herein as $FP_{18}$. However, the actual content and arrangement of a particular set of imaging optics can vary.

A patterned semiconductor wafer 12 featuring a plurality of wafer dies 14, is placed and aligned on a continuous moving XY translation stage 16 to impart motion between the wafer and the components used to image the wafer. XY translation stage 16 moves wafer 12 typically in a serpentine pattern beneath an optical imaging system 18, thereby changing which area of the wafer is in view of the imager. However, movement patterns other than a serpentine pattern could be used. Additionally, the wafer may be moved in a different manner in other embodiments. Furthermore, in some embodiments, the wafer may remain stationary, with apparent motion between the wafer and component(s) used to image the wafer imparted by the use of one or more optical components. For instance, a rotating mirror can be used to move the field of view of imaging optics 18 in a serpentine (or other) pattern across the wafer. In other embodiments, relative motion may be imparted by moving both the wafer and adjusting optical components.

Movement of XY translation stage 16 (and therefore movement of wafer 12) is synchronized with action of a multi-component camera system by a central control system 20 via control/data links 22, in such a way that wafer 12 moves the equivalent of one field of view 24 during a CCD matrix photo-detector frame time. For example, the frame time and motion may be synchronized so that the wafer moves only on the order of about $10^{-2}$ of a single pixel during exposure to an illumination system 26, thereby resulting in little to no image smear or loss of image resolution.

In this example, illumination system 26 includes a repetitively pulsed laser 32, a laser beam expander 34, a laser beam light path 36, control/data links 38, and a crystal 40 having non linear optical properties and serving as a 'second harmonic' generating crystal. This type of illumination system enables ultra fast imaging of a large field of view 24, by featuring pulsed laser 32 for repetitively generating and propagating a highly bright and highly energetic light pulse in an extremely short period of time. Illumination system 26 is in communication with the central control system 20 via control/data links 38. Of course, image splitting in accordance with the present subject matter can be used in any inspection system regardless of the particular type, mode, or manner of illumination.

Briefly, FIG. 16 illustrates exemplary components associated with illuminating an object in an inspection system. According to different methods of operation, three alternative modes of illumination can be provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination may be preferred. In order to detect a small particle on a surface, DF illumination can generally yield better results.

In bright field illumination in general, the illumination is incident on the sample through the same objective lens as is used for viewing the sample. FIG. 16 shows a bright field illuminating laser source 1300 delivering its output beam 1015 into an optical delivery fiber bundle 1021, preferably by means of a laser to fiber coupler 1150. This optical fiber bundle 1021 provides both uniform illumination on the sample and coherence breaking of the laser illumination. In some embodiments, only a single fiber bundle is used, but it is to be understood that a serially-arranged fiber bundle solution may also be suitable. In other embodiments, one or more bundles may be combined with further components, such as a light guide or guides. Discussion of exemplary fiber/light guide combinations can be found in co-pending U.S. patent application entitled "Speckle Reduction Using a Fiber Bundle and Light Guide," Ser. No. 11/503,859, filed Aug. 14, 2006, and incorporated by reference herein for all purposes.

From the output termination of the fiber bundle 1021, the laser beam is imaged by means of illumination transfer lenses 301, 302 onto the objective lens in use 1201, which is operative to focus the illumination onto a wafer 1100 being inspected. Appropriate alternative objective lenses 1201' can be swung into place on an objective revolver 1200, as is known in the microscope arts. The illumination returned from the wafer is collected by the same objective lens 1201, and is deflected from the illumination path by means of a beam splitter 1202, towards a second beam splitter 1500, from where it is reflected through the imaging lens 1203, which images the light from the wafer onto the detectors of the imager, with one of the detectors represented in FIG. 16 at 1206. In this example, only a single detector and optical path is shown for purposes of example. In practice, the path of light comprising the split portions of the inspection image will, of course, vary. In this example, the second beam splitter 1500 is used to separate the light going to the imaging functionality from the light used in the auto-focus functionality, which is directed by means of the auto-focus imaging lens 1501 to the auto-focus detector 1502.

When conventional dark field illumination is required for the imaging in hand, a dark field side illumination source 1231 is used to project the required illumination beam 1221 onto the wafer 1000. When orthogonal dark field, or obscured reflectance dark field illumination is required for the imaging in hand, an alternative dark field illumination source 1230 is used to project the required illumination beam 1232 via the obscured reflectance mirror 1240 onto the wafer 1000 orthogonally from above. FIG. 16 indicates sources 1300, 1231, and 1230 at different locations. However, any or all of sources 1300, 1230, and 1231 may comprise the same light source, with the bright field, dark field, and obscured reflectance dark field effects achieved through moving the source(s) and/or redirecting illumination to the appropriate angle using one or more optical components. Further, it is to be understood that other arrangements for laser illumination and/or other illumination methods entirely could be used in conjunction with the present subject matter.

In operation, one or more images of the wafer are obtained and the images are analyzed to determine the presence or absence of a defect or potential defect in the wafer. For example, the tool may include an image analysis system comprising one or more computers or other suitable image processing hardware configured to evaluate the images. In the example of FIG. 15, an image processing system 100 includes parallel configured image processing channels 90 for image grabbing by an image grabber 92, an image buffer 94, a defect detection unit 96, a defect file 98, and control/data links 102. Image data acquired by focal plane assembly 30 featuring twenty-four two-dimensional CCD matrix photo-detectors 52 is processed in parallel, whereby each of the twenty-four CCD matrix photo-detectors 52 communicates separately, in parallel to the other CCD matrix photo-detectors 52 of focal plane assembly 30, with image grabber 92, via twenty-four separate image processing channels 90. Instead of processing image data using a single serial channel of 48 megapixels at a CCD frame speed acquisition rate of 30 times per second, resulting in a single channel with a very high, 1.5 gigapixels per second processing rate, each of the twenty-four separate image processing channels 90 having about 2 megapixels of image data, acquired at a rate of 30 times per second, is used for processing at a moderate rate of 60 megapixels per second. Image processing system 100 is in communication with central control system 20 via control/data links 102

As another example, the tool may be connected to suitable hardware, or image data may be provided to suitable hardware in any other manner for later analysis.

Any suitable type(s) of analysis may be used to determine the presence or absence of defects. For example, the tool may obtain images on a frame-by-frame basis and compare single frames or groups of frames to references. As another example, the tool may analyze images without comparison to other images, such as locating bright spots on a dark area and/or dark spots on a light area. Any suitable comparison/analysis technique(s) may be used, including cell-to-cell comparison, die-to-die comparison, and may be carried out using any suitable software algorithm(s) and/or specialized hardware to analyze and process the images.

The above discussion is for purposes of example only with regard to illumination and imaging techniques. The present subject matter can be utilized in the context of any suitable inspection tool. Next, several different embodiments of splitting techniques and splitting apparatus will be discussed. The splitting apparatus can be used to obtain the continuous surface of detectors illustrated above as focal plane assembly 30.

Figure 1:
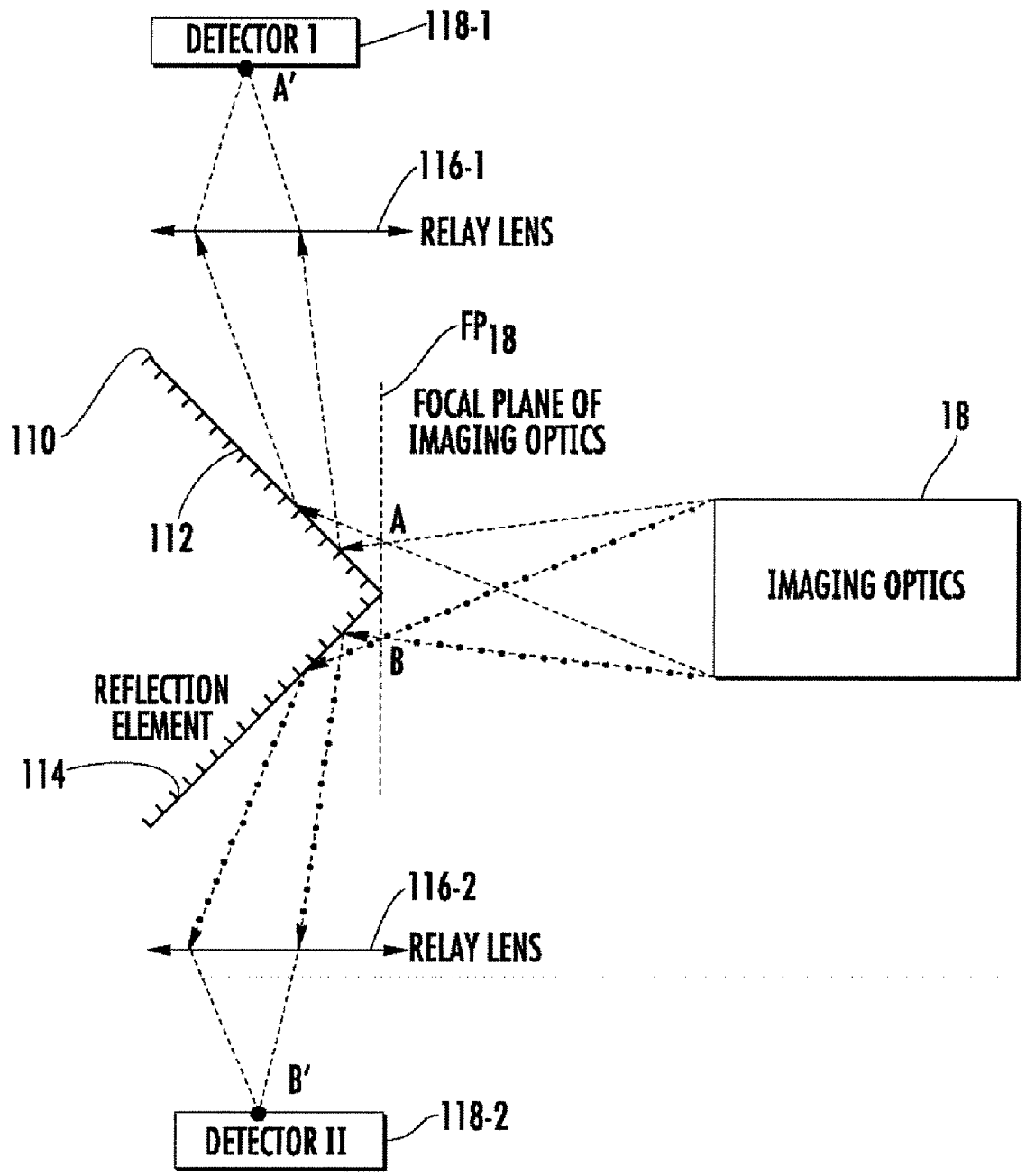
FIG. 1 is a diagram illustrating an exemplary embodiment of a splitting apparatus comprising a plurality of reflective planes.
Figure 2:
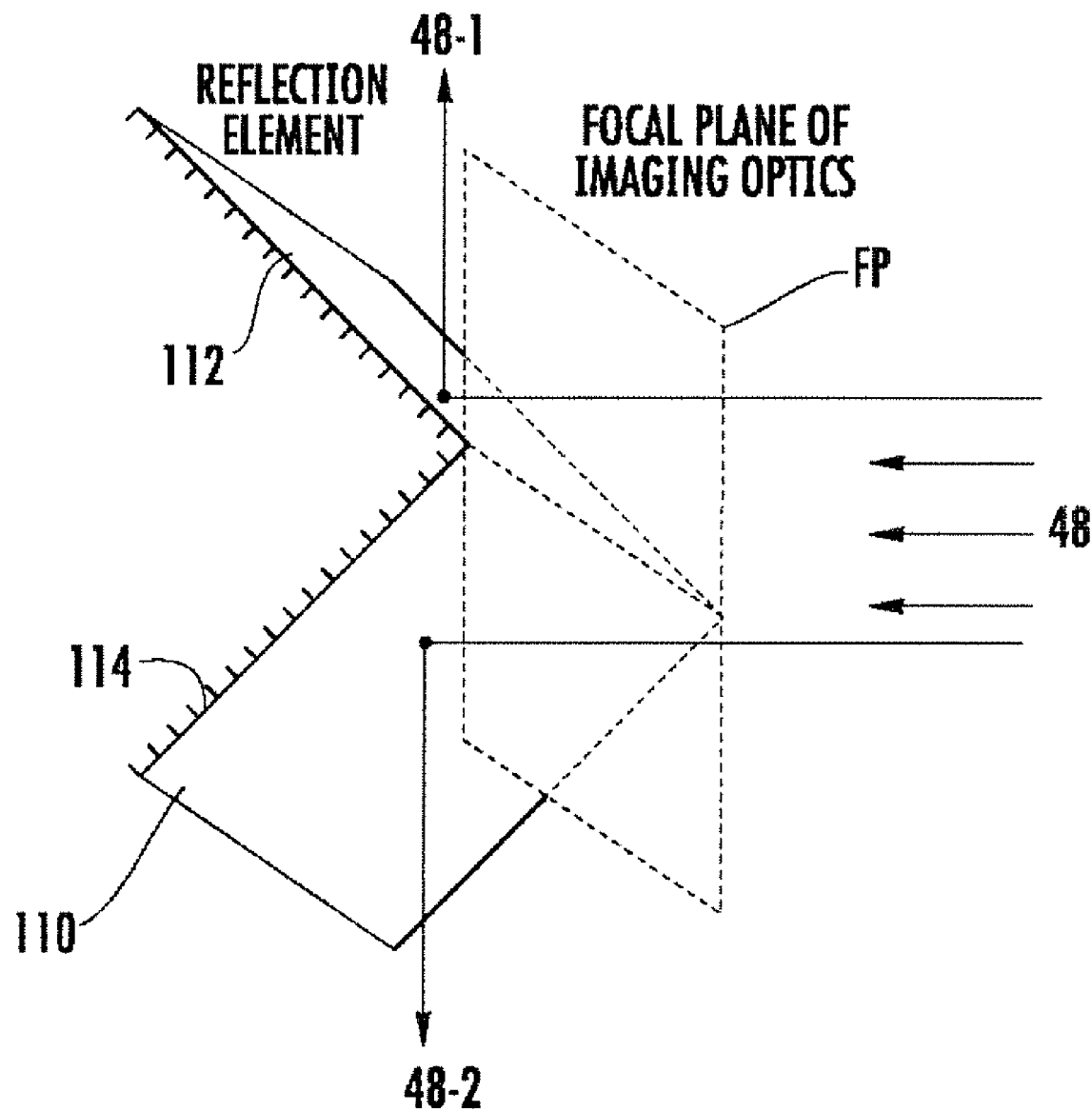
FIG. 2 is a partial perspective view of the splitting apparatus of FIG. 1.

FIG. 1 shows a top view of a first exemplary embodiment 110 of a splitting apparatus of the present subject matter. A reflection element is constructed from two reflecting planes 112 and 114 placed so the contact between the reflecting planes is at the focal plane $FP_{18}$ of the inspection tool's imaging optics 18. A 3-Dimensional view of the arrangement of the reflecting element and the focal planes is shown at FIG. 2. The dotted line represents part of the reflection element that is behind the focal plane in the drawing.

Detectors 118-1 and 118-2, along with respective relay lenses 116-1 and 116-2 are placed to image the focal plane on the detectors on each side of the reflecting element relative to the intersection of planes 112 and 114 with $FP_{18}$. Each ray that enters each side of the focal plane is therefore passed by a reflecting element to the corresponding detector. Therefore, there is no degradation of the intensity or its uniformity and the angular distribution remains.

The contact between the parts of the reflecting element preferably is as small as possible to decrease the possibility of obscuring portions of the image or other effects. When two-dimensional detectors are used, preferably the size of the contact area is less that one pixel width on the detector after imaging by the relay lens.

In FIG. 1, the two dotted rays from the imaging optics are focused on point B in the focal plane of imaging optics 18. The two rays continue to the reflecting element 114 and are reflected toward the relay lens 116-2. Relay lens 116-2 focuses the rays again at point B' on detector 118-2. Thus, point B' is the image of the point B. The dashed rays indicate ray paths for the top part of the focal plane and which are directed towards the top detector 118-1. This configuration images the bottom half of the focal plane to detector 118-2 and the top part of the focal plane to detector 118-1.

Figure 3:
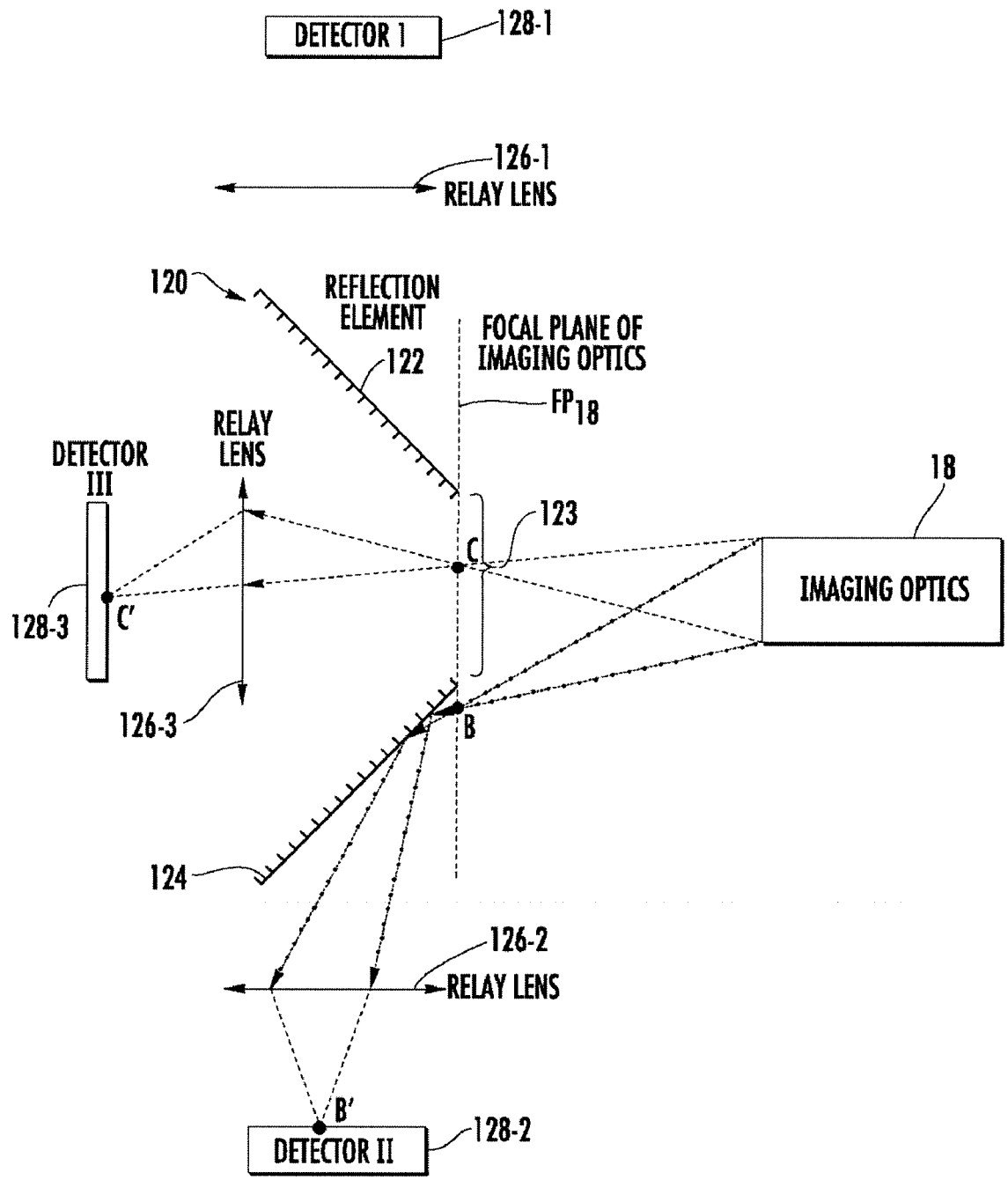
FIG. 3 is a diagram showing an exemplary embodiment of a splitting apparatus comprising a plurality of reflective planes separated by a gap.

Turning now to FIG. 3, an exemplary embodiment of a splitting apparatus 120 is discussed. In this example, an image is split into three parts. In this case, the two reflecting planes 122 and 124 (i.e. reflection elements) are separated by a gap 123 at focal plane $FP_{18}$. The rays reflected from the first reflecting plane 122 are imaged on a first detector 128-1 via relay lens 126-1 and the rays reflected from the second reflecting plane 124 are imaged on second detector 128-2 via relay lens 126-2. In this embodiment, the rays that pass through gap 123 at the focal plane $FP_{18}$ defined by the edges of planes 122 and 124 are imaged by a third detector 128-3 via relay lens 126-3.

The two dotted-line rays act as in the two-way image splitting of the example above. However, the two dashed rays exit from imaging optics 18 and are focused on point C in the focal plane $FP_{18}$ of the imaging optics. The rays continue through the separated area toward the relay lens 126C of detector 128C. The relay lens focuses the rays again at point C' on detector 128C. Thus, point C' is the image of the point C.

Figure 4:
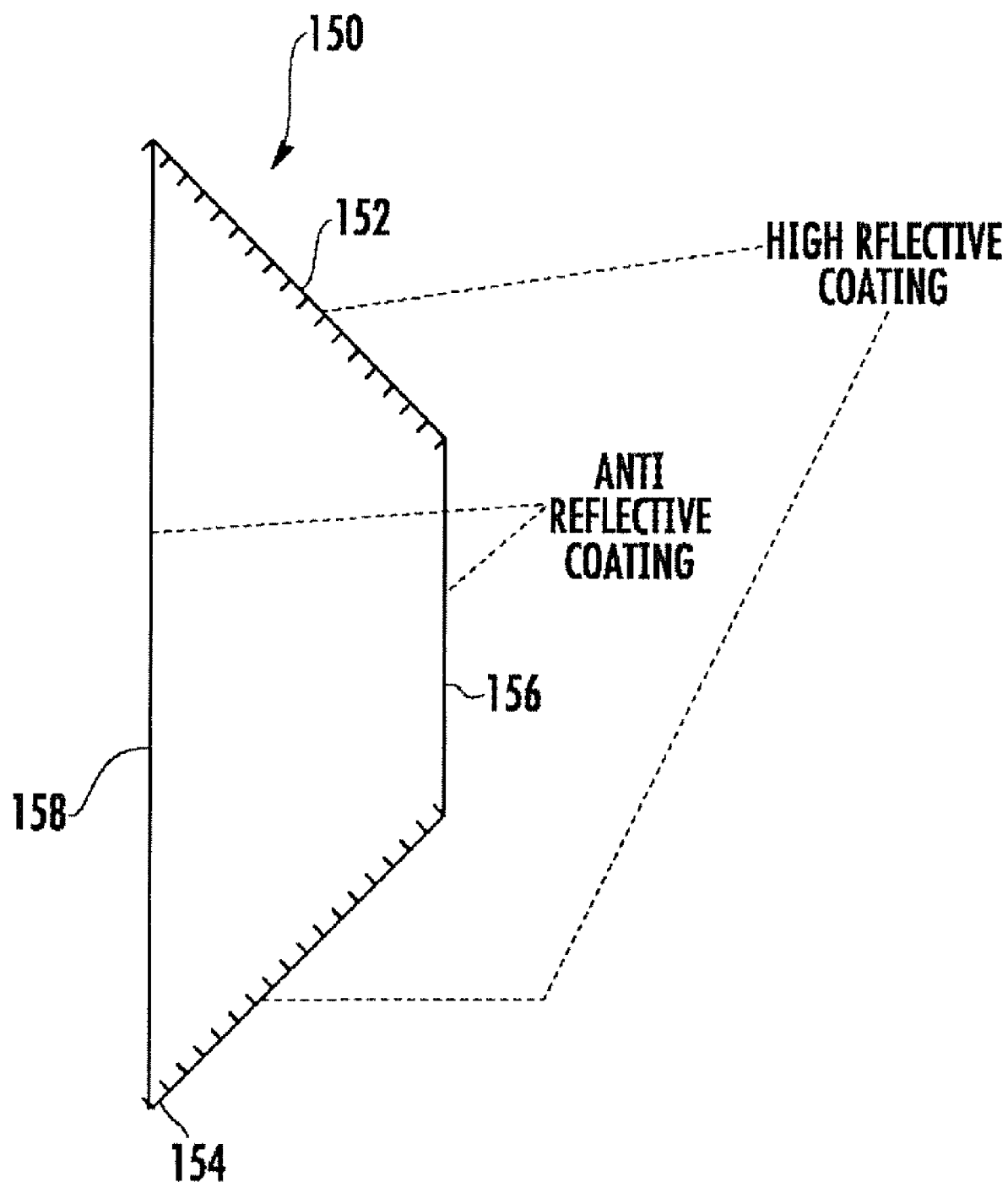
FIG. 4 is an example of a splitting apparatus which may be used to obtain the effects of a gap by way of a single optic element.

Although this example shows separate components, the reflective planes and the gap may be three facets of a single optic element 150 as illustrated in FIG. 4. For instance, sides 152 and 154 (corresponding to planes 122 and 124 of the example in FIG. 3) may comprise highly reflective coatings, while the transmitting side 156 (corresponding to the gap 123 of FIG. 3) may be coated with an anti reflecting coating. The back plane 158 of element 150 may be also coated with anti reflective coating. The body of element 150 may comprise any suitable material, such as glass. Although referred to as a "single optic element," it will be understood that multiple components could be assembled into a single optical element.

Figure 5:
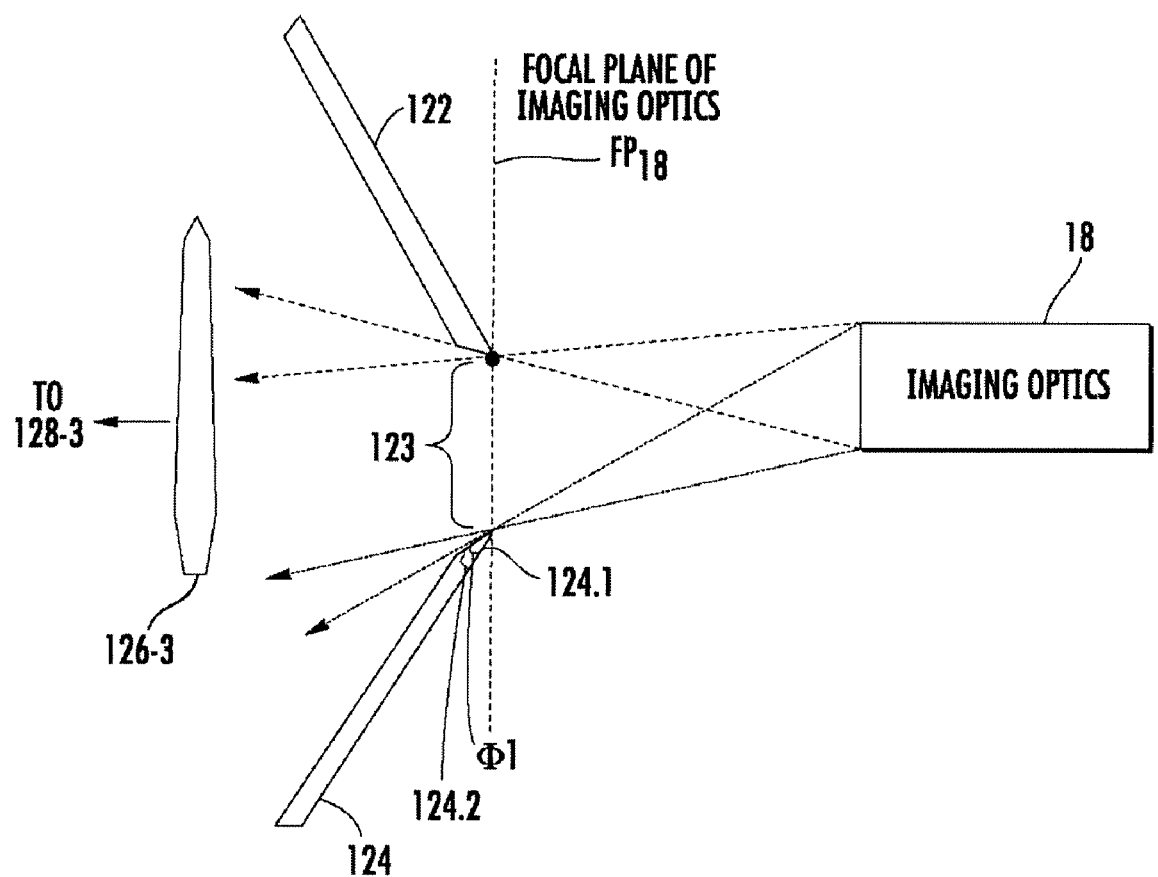
FIG. 5 is a top view of the splitting apparatus of FIG. 3, including an exemplary modification so that the edges of the reflective elements bordering the gap comprise acute angles to minimize interference with light passing through the gap.
Figure 5A:
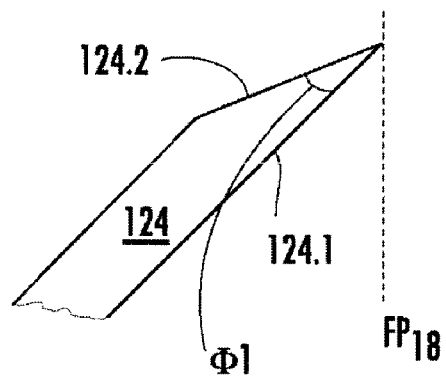
FIG. 5A is a close-up view of one exemplary element comprising a reflective plane used in the splitting apparatus as shown in FIG. 5 and further illustrating the an acute angle.

In embodiments featuring splitting at one or more gaps, the angle of the edge of the reflecting plane elements should be acute in order not to block rays for the detector(s) receiving light that passes through the gap. Generally, the edge angle of either element comprising a reflecting plane should be formed or configured so that light emanating at extreme angles from the imaging optics will not impinge the reflecting plane. FIG. 5 is a top view of the splitting apparatus of FIG. 3. In the example of FIG. 5, portions 124.1 and 124.2 define an edge angle (d) of the reflective element comprising reflective plane 124. For example, the element may comprise a mirror, with portions 124.1 and 124.2 comprising respective portions that face toward and away from focal plane $FP_{18}$. This can be seen in closer detail in FIG. 5A, which is a zoomed-in view of the element comprising reflective plane 124 at $FP_{18}$. Back portion 124.2 can be ground, cut, or otherwise shaped to allow rays to pass through gap 123 with little or no interference from the body of the element comprising reflective plane 124. The element comprising reflective plane 122 may be formed or configured in a similar manner.

Figure 6:
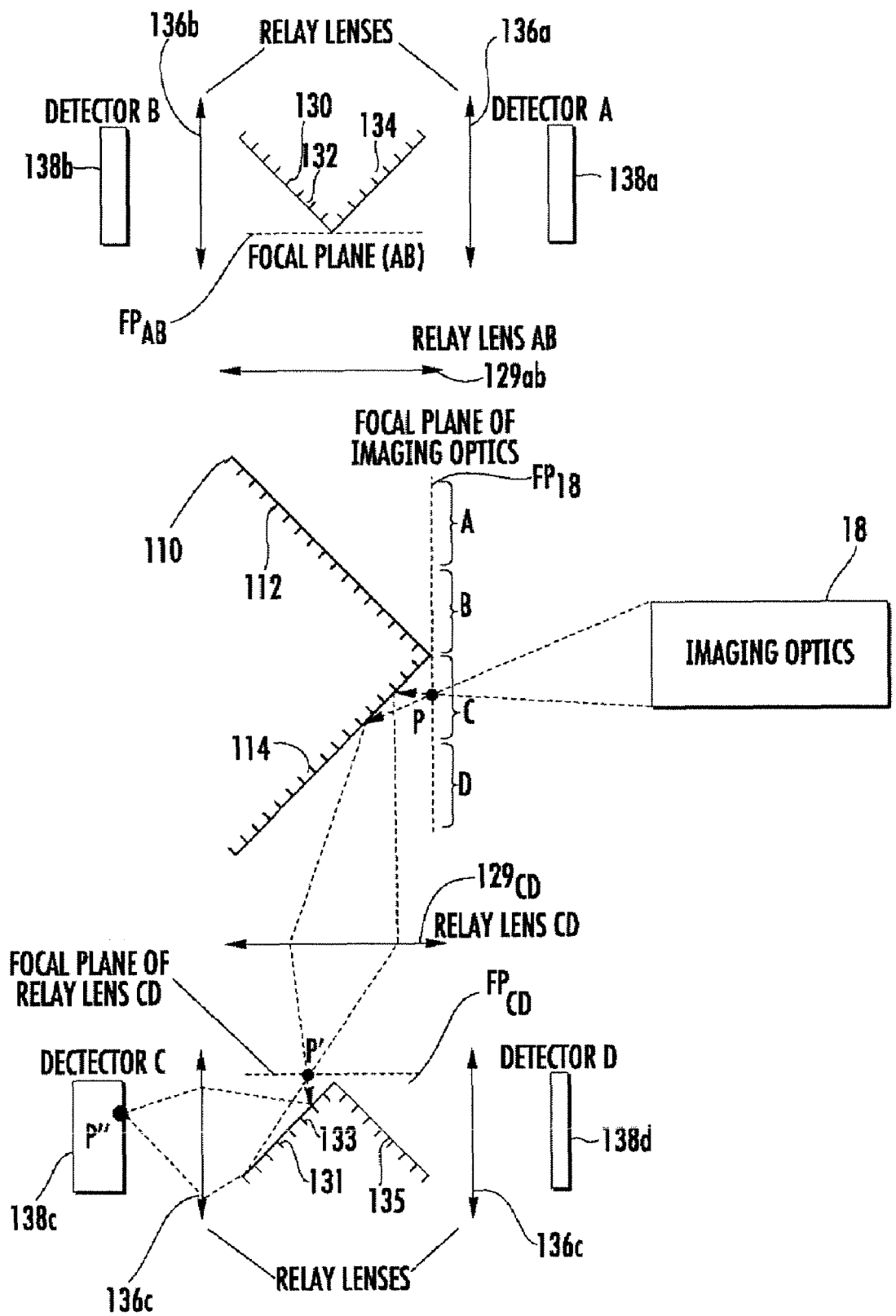
FIG. 6 is a diagram showing an exemplary embodiment of a splitting apparatus comprising two reflective planes which are cascaded with two additional splitting apparatuses.

In some embodiments, multiple splitting apparatuses of the same type or of different types can be used to split an image into multiple portions. For instance, FIG. 6 shows an example where reflective plane structures are cascaded. Specifically, in this example, there is a cascading of two two-way image splits. The first splitting apparatus 110 splits the image to two parts (left and right, for instance) using reflective planes 112 and 114. Each of those parts is split again to two parts by a respective splitting apparatus illustrated as 130 (comprising planes 132 and 134) and 131 (comprising planes 133 and 135). Each second splitting apparatus 130, 131 is positioned at a respective focal plane $FP_{AB}$ and $FP_{CD}$ corresponding to relay lenses $129_{AB}$ and $129_{CD}$. The four sections of the image at the focal plane $FP_{18}$ of the imaging optics 18 (illustrated as A, B, C and D in FIG. 6) are each imaged into the respective detectors 138A, 138B, 138C, and 138D after the double splitting.

FIG. 6 includes an example ray trace for two rays that exit imaging optics 18 and are focused on point P in the focal plane $FP_{18}$. The rays impinge the reflective plane 114 of the first splitting element 110 and are reflected toward relay lens 129-CD. This lens focuses the rays at point P' on the focal plane of the lens (FPCD). Then, the rays impinge a reflective plane 133 of the second splitting apparatus 131 and reflected toward another relay lens 136C. Lens 136C focuses the rays at point P'' on detector 138C. P'' is the image of P' which is the image of P. Therefore, P'' is the image of P.

The cascaded splitting may be in different image dimensions. For example the first split may split the image into left and right portions, and the second split may divide each of those portions into top and bottom. In that case the original image is split to 2×2 quadrants (top-left, top-right, bottom-left and bottom-right). A cascade resulting in 9 portions (i.e. 3×3 parts), may be created by splitting an image three ways in the horizontal axis (i.e. split into left/middle/right portions) while splitting each of those parts three ways in the vertical axis (i.e. split into top/center/bottom portions).

In this example, the cascade comprises splitting apparatus of the same type. However, any splitting element may be cascaded with other kind of splitting elements, such as beam splitters, mirrors not in the focal plane, etc as is known in the art. Furthermore, the cascades are not limited to two levels. Any number of elements may be cascaded.

Figure 7:
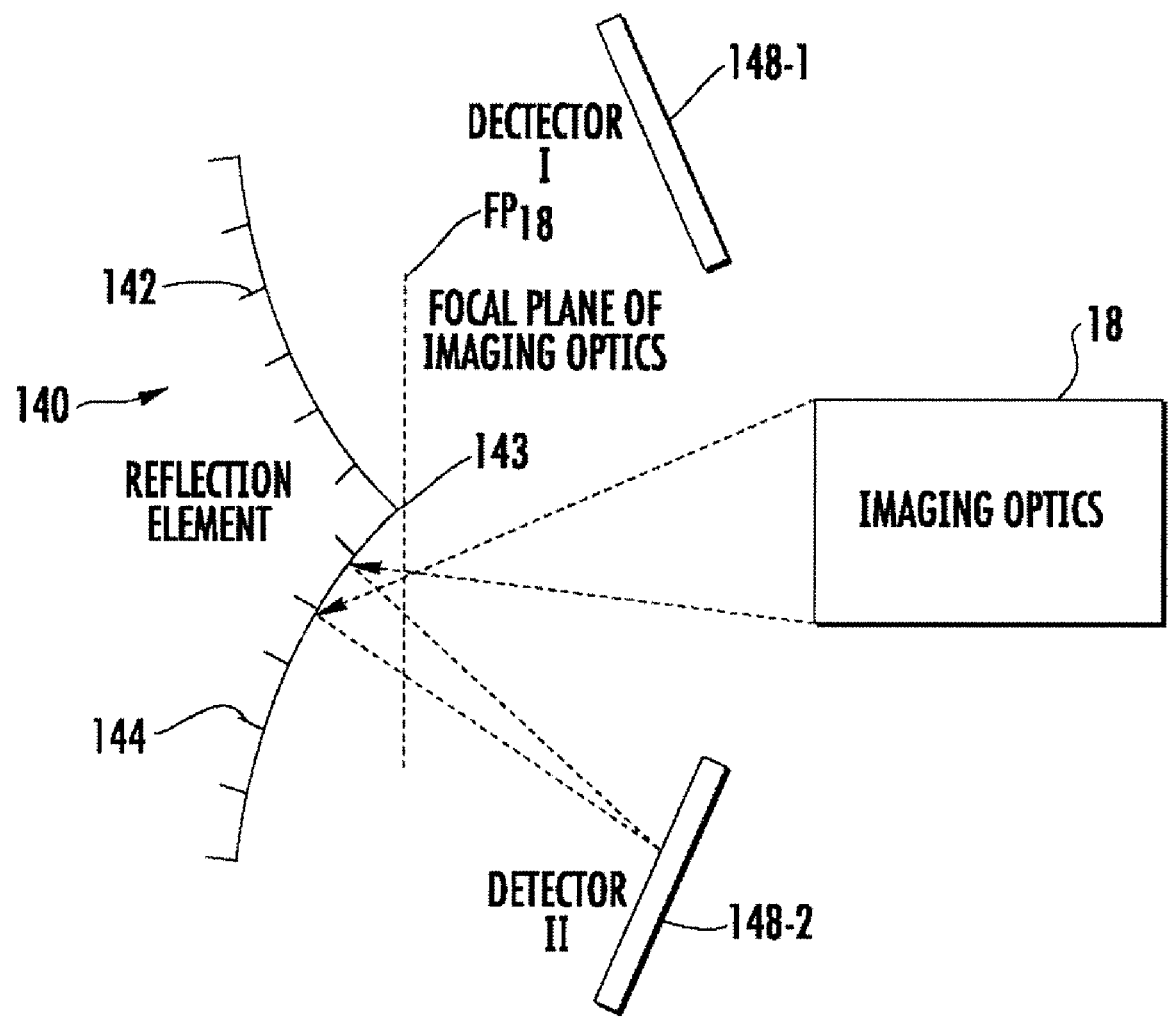
FIG. 7 is a diagram showing an exemplary embodiment of a splitting apparatus comprising curved reflective planes.

In some embodiments, one or more of the reflective elements may be curved in order to avoid using the relay lens or to simplify the relay lens. For example, FIG. 7 shows an exemplary splitting apparatus 140 comprising two reflective planes 142 and 144 meeting at a tip 143 positioned at focal plane $FP_{18}$. Rays for each part of the image are reflected from the reflecting element and focused directly on respective detectors 148-1 and 148-2 without the need for relay lenses in this example. The curved reflecting element may be of any type, including spherical, elliptic, parabolic, or of a general curvature. This type of plane may be suitable for splitting into two, three, or more images, and may be cascaded.

Figure 8:
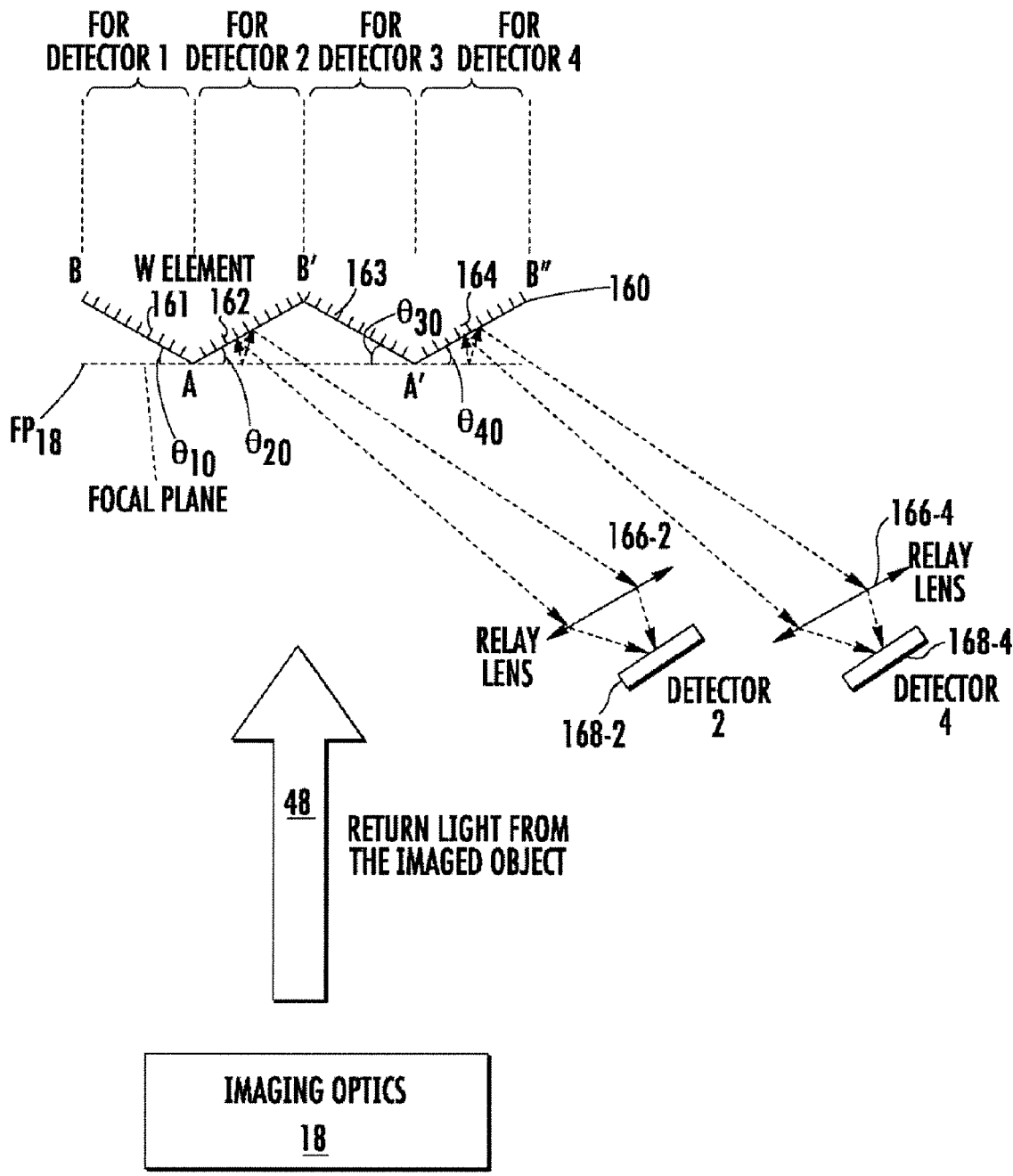
FIG. 8 is a diagram showing an exemplary embodiment of a splitting apparatus comprising a "W" shaped element.

Turning now to FIG. 8, an exemplary splitting apparatus 160 comprising a "W" element will be discussed. In this example, a plurality of elements comprising reflective planes 161, 162, 163, and 164 are arranged so to form a "W" shape, with the tips of the "W" (points A and A' in FIG. 8) positioned at focal plane $FP_{18}$. In this example, splitting apparatus 160 directs light 48 comprising the image of the inspected object to four different detectors, two of which (168-2 and 168-4) are shown in FIG. 8. In this example, light reflected by reflective plane 162 is directed to detector 168-2 via relay lens 166-2, while light reflected by plane 164 is directed to detector 168-4 by relay lens 166-4.

Figure 9:
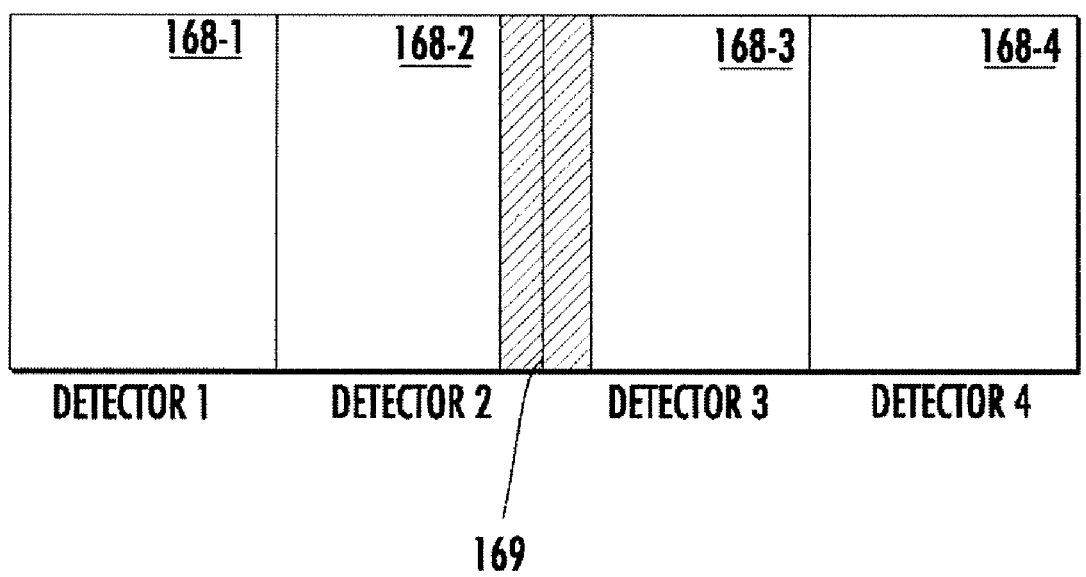
FIG. 9 is an illustration showing a hypothetical area of non-uniformity which may occur in some embodiments using a "W"-shaped splitting apparatus.

In this embodiment, the image is split into the four portions labeled in FIG. 8. The split between planes 161 and 162 and the split between planes 163 and 164 generally does not result in non-uniformity at the detector plane, since the splitting occurs at focal plane $FP_{18}$. However, the slit between planes 162 and 163 does not occur at the focal plane. Accordingly, there is some non-uniformity between detectors 168-2 and 168-3 (not shown in FIG. 8). FIG. 9 illustrates a continuous surface of detectors 168-1 and 168-4 resulting from the focal plane assembly comprising splitting apparatus 160. FIG. 9 represents a view of the combined detector area which would be seen, for instance, by an observer viewing focal plane $FP_{18}$. In FIG. 9, the area of non-uniformity is shown at detectors 168-2 and 168-3 using cross-hatched area 169.

Although the example of FIG. 8 splits an image into four parts, multiple "W" shapes may be used to split an image into more parts. For example, adjacent "W" shapes could be used, such as a "WW" shape to split an incoming image into 8 portions. As another example, one or more "W" shapes may be used in conjunction with a "V" shape, such as a "WV" arrangement which splits an incoming image into six portions. Other W-V combinations (e.g., "VWW", "VWWV," etc.) could be used.

Furthermore, the angles $\Theta_{10}$, $\Theta_{20}$, $\Theta_{30}$, and, $\Theta_{40}$, representing the angle between each reflective plane and focal plane $FP_{18}$, can vary. For instance, in this example, the magnitude of each angle $\Theta$ is approximately 20 degrees. As $\Theta$ decreases, the area of non-uniformity caused by splitting past focal plane $FP_{18}$ decreases. However, by reducing $\Theta$, the distance to the respective relay lenses increased, which can require larger relay lenses and longer optics.

In some embodiments, the "W" element may be positioned so that $FP_{18}$ passes through the reflective planes (i.e. with points A and A' lying on the opposite side of $FP_{18}$ from points B, B', and B''). In that case, areas of non-uniformity will occur between each pair of detectors. However, the maximum size of a single non-uniform continuous area will be smaller than the case where $FP_{18}$ passes through points A and A'.

In still further embodiments, the "W" element may be two-dimensional, such as by using quadrangular pyramids.

Figure 8A:
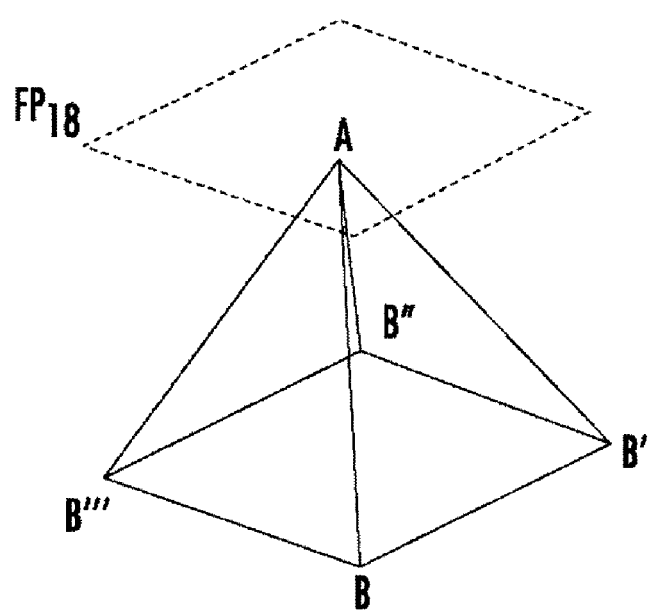
FIG. 8A is a diagram showing an exemplary implementation of a "W"-shaped element using a pyramidal prism.

An example of a pyramid-shaped element is shown in FIG. 8A, which depicts a quadrangular pyramid having an apex "A" which intersects with $FP_{18}$ and base vertices B, B', B", and B'". Light impinging on each face is directed to a respective detector. In this embodiment, areas of non-uniformity will also exist between the detectors, with the non-uniformity becoming wider near points B, B', B", and B'" since such points represent the maximum distance from the focal plane. In other embodiments, the pyramid-shaped element could be positioned with $FP_{18}$ laying between A and points B, B', B", and B'".

As was mentioned above, in some embodiments, images may be split by cascading various splitting apparatuses. For instance, one "W" element may split an image into four potions, with each portion split by a respective "W" element for a total of sixteen portions. In such embodiments, fewer areas of non-uniformity will occur as compared to the case where four "W" elements are positioned at the focal plane (i.e. when a "WWWW" element is used). This is because when four "W" elements are used, there are seven splits not at the focal plane producing seven non-uniform areas. In contrast, when cascaded "W" elements are used, there is one area of non-uniformity from the initial split, and one non-uniformity for each "W" that receives one of the portions of the initial split, for a total of five areas of non-uniformity.

Figure 10:
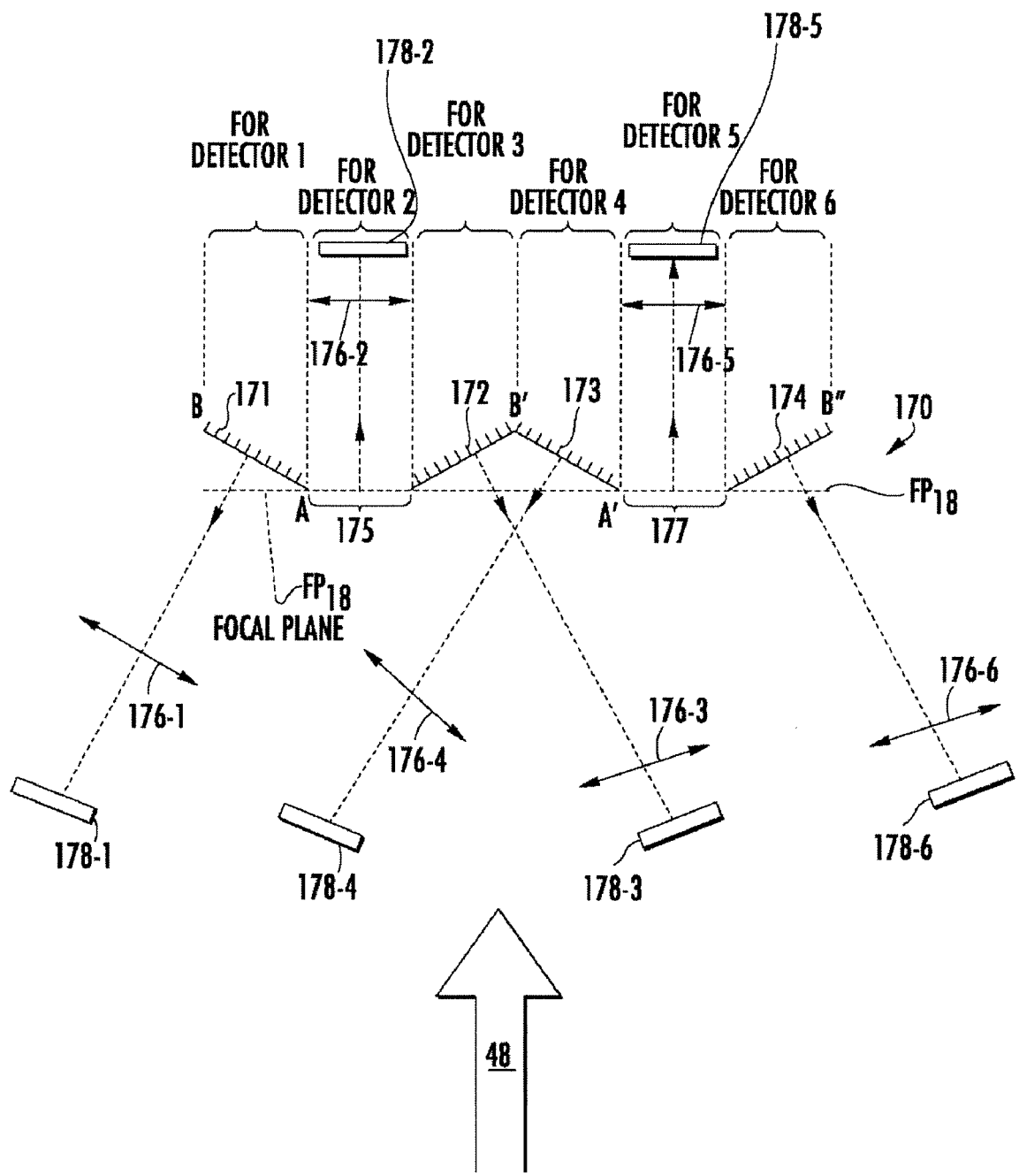
FIG. 10 is a diagram showing an exemplary splitting apparatus comprising a "W" shaped element which is separated by a plurality of gaps.

Another embodiment of a splitting apparatus is shown in FIG. 10, which shows splitting apparatus 170 which comprises a "W" element featuring gaps at focal plane $FP_{18}$. In this example, incoming light 48 is split into six portions. Two portions pass through respective gaps 175 and 177 to detectors 178-2 and 178-5 via relay lenses 176-2 and 176-5. The remaining portions are respectively reflected by reflective planes 171, 172, 173, and 174 to detectors 178-1, 178-3, 178-4, and 178-6 via relay lenses 176. Only one area of non-uniformity exists in this example: the non-uniformity will lie between detectors 178-3 and 178-4 due to the split that occurs past focal plane $FP_{18}$ between reflective planes 172 and 173. As was noted above, the area of non-uniformity can be minimized by reducing the angle between the reflective planes and the focal plane and/or by the shape of the edges of the reflective planes that are positioned at focal plane $FP_{18}$.

Figure 11:
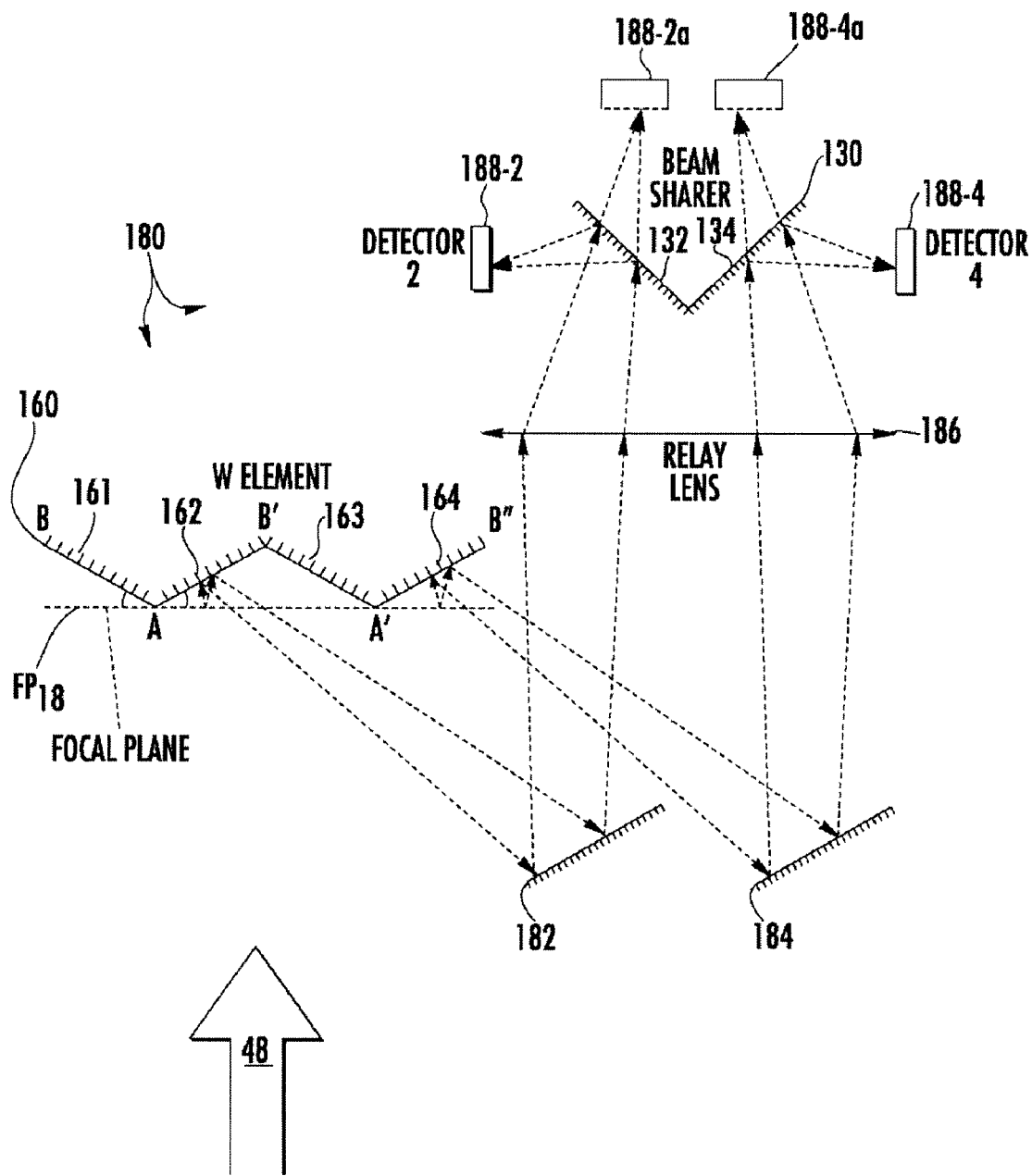
FIG. 11 is a diagram showing an exemplary splitting apparatus comprising a "W" shaped element and additional components whereby a plurality of detectors can share a relay lens.

FIG. 11 illustrates another exemplary configuration of a splitting apparatus. In this example, splitting apparatus 180 comprises a "W" shaped element 160. Reflective planes 161, 162, 163, and 164 are positioned relative to $FP_{18}$ as in the previous example of FIG. 8. However, in this embodiment, additional components are included so that a single relay lens 186 can be used for detectors 188-2 and 188-4.

In this particular example, a splitting apparatus 130, comprising reflective planes 132 and 134, is used as a beam sharer. Mirrors 182 and 184 are used to direct rays from respective reflective planes 162 and 164 toward beam sharer 130 via relay lens 186. Thus, a single relay lens can be used. Beam sharer 130 directs rays to respective detectors 188-2 and 188-4. Beam sharer 130 does not introduce non-uniformities since the rays reflected by planes 162 and 164 do not overlap with one another. In other embodiments, though beam sharer 130 may be omitted by positioning detectors 188-2 and 188-4 adjacent to one another. These alternate locations are shown at 188-2A and 188-4A. Preferably, each detector is separated by an area essentially equal to a field of view to avoid any potential overlap.

A similar arrangement with or without the use of a beam sharer could be used to direct light to detectors 188-1 and 188-3 (not shown in this example) using a single relay lens.

Figure 12:
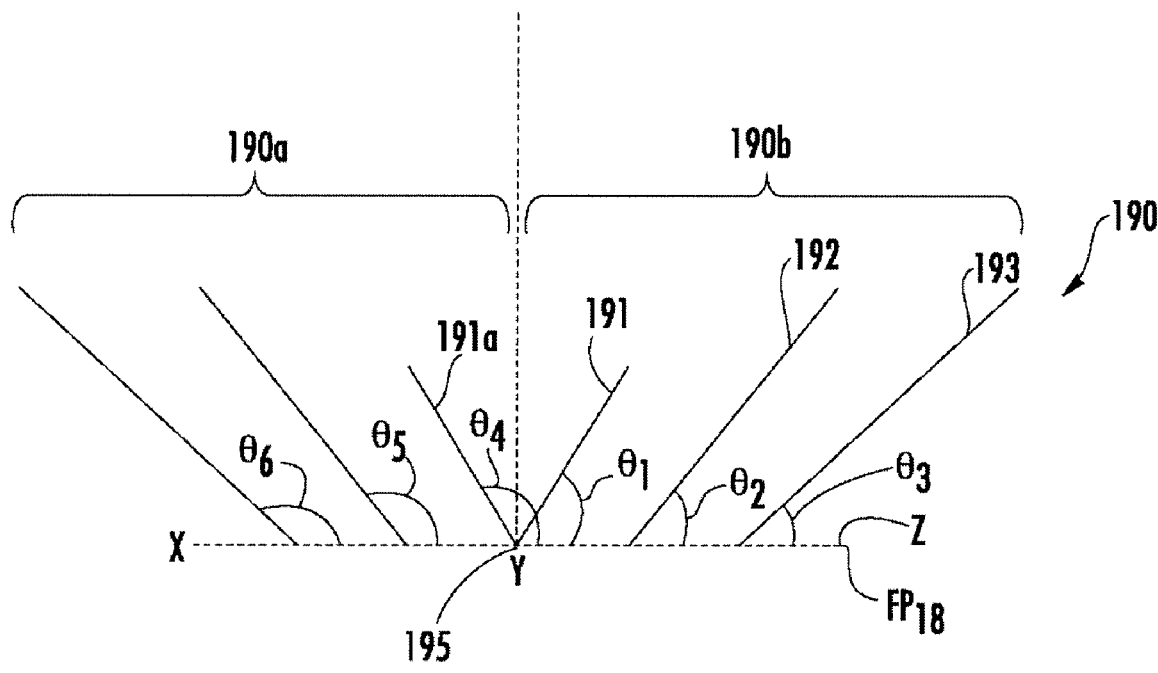
FIG. 12 is a diagram showing an exemplary splitting apparatus comprising a fan-like assembly.
Figure 13:
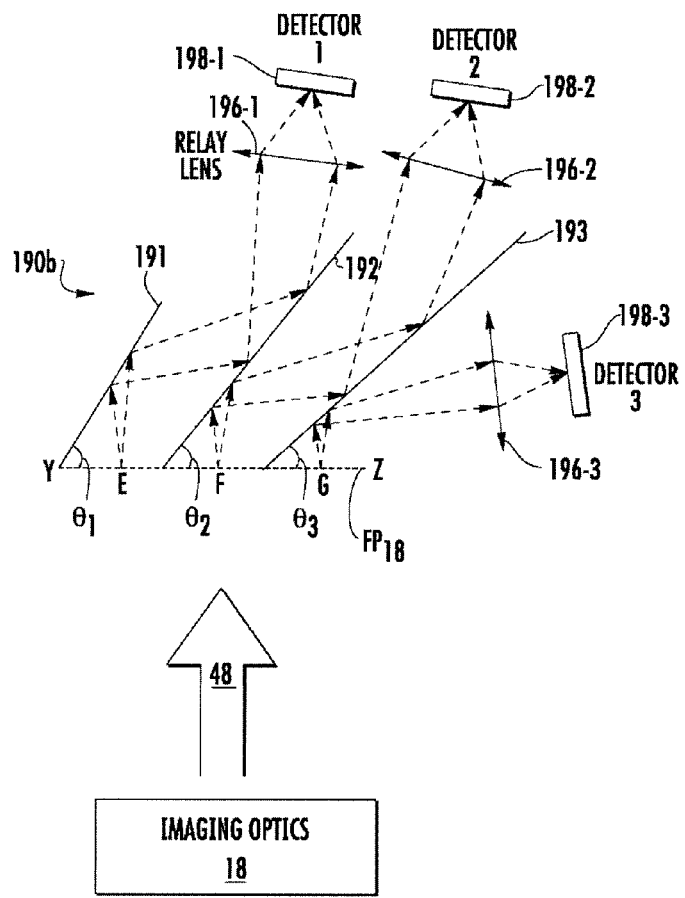
FIG. 13 is a diagram showing an exemplary fan-like assembly, in this example one of two portions forming the assembly of FIG. 12.

Turning now to FIGS. 12 and 13, another exemplary splitting apparatus will be discussed. Splitting apparatus 190 of these examples comprises a fan-shaped assembly of reflective planes which can split returned light 48 into four or more portions without image intensity loss or creation of zones of non-uniformity. In this example, splitting apparatus 190 comprises two parts 190a and 190b which are symmetrical about a center line of focal plane $FP_{18}$. However, in other embodiments, a splitting apparatus may comprise non-symmetrical fan shapes, or may comprise a single portion such as 190a or 190b alone.

FIG. 13 shows portion 190b in closer detail. Generally, the fan comprises an arrangement of generally planar reflective elements, such as mirrors, that are reflective on two sides. The magnitude of the fan angle θ defined by the focal plane and the reflective element varies amongst the reflective elements along the length of the focal plane. Namely, as between any two elements, the angle θ of the element closer to the second end of the focal plane is less than the angle θ of the element farther from the second end. Put another way, the fan angles monotonically decrease along the length of the focal plane in one direction and increase in the other. In the example of FIG. 13, $\Theta_1 > \Theta_2 > \Theta_3$, with the first end of the focal plane defined by point Y and the second end defined by point Z. Returning briefly to FIG. 12 and portion 190a, the first end would correspond to point X and the second end would correspond to point Y, with $\Theta_6 > \Theta_5 > \Theta_4$. Across the length X-Z of the entire assembly of this example, $\Theta_6 > \Theta_5 > \Theta_4 > \Theta_1 > \Theta_2 > \Theta_3$.

The rays that are reflected by the side of each element facing the focal plane are reflected again by the reflective plane at the back side of the adjacent element, with the "back side" referring to the side of an element that faces away from the focal plane. However, the rays reflected by the front side of one or more elements not adjacent to the back side of another element are reflected once and then into a detector with no backside reflection. Thus, in this example, the rays at point E of $FP_{18}$ are first reflected by the front reflective plane of element 191 and then by the back side of element 192 into detector 198-1 via relay lens 196-1. Similarly, the rays at point F are reflected by the front side of element 192, the back side of element 193, and then into detector 198-2 via relay lens 196-2. The rays at point G are reflected once by the front side of element 193 into detector 198-3 via relay lens 196-3.

Generally, the reflective element positioned adjacent to the element that is nearest the second end of the focal plane (192 in the example of FIG. 13) should be positioned with an angle of at least 45 degrees+the numerical aperture (NA) of incoming light beam 48. The fan assembly can be used to split to more or fewer potions than the six portions of FIG. 12 or the three portions of FIG. 13. The maximum number of portions generally depends on the NA of the incoming beam, with a smaller NA corresponding to a greater potential number of portions.

As was noted in earlier examples, a gap or hole can be used to reduce or avoid non-uniformities between adjacent detectors. For instance, in FIG. 12, elements 191 and 191a intersect at 195 (also corresponding to point Y at $FP_{18}$). A gap could be placed between elements 191 and 191a with a corresponding detector or detectors positioned behind the fan assembly. Although the fan assembly may advantageously allow for splitting images into multiple portions, each image portion generally should have its own relay lens. Since the rays reflected from each element are directed at different angles to one another, a combined relay lens for multiple elements can be difficult to implement.

Figure 13A:
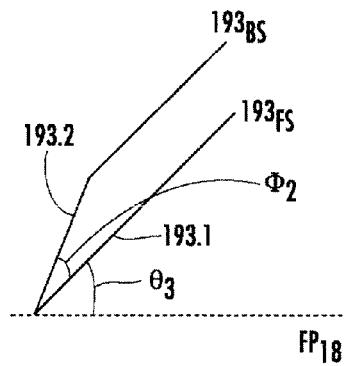
FIG. 13A is a close-up view of the positioning of one reflective element comprising reflective planes used in the fan assembly of FIG. 13 and illustrating the use of an acute angle to minimize interference at the gap between elements.

As was noted earlier with respect to FIG. 5, it can be advantageous to shape the edge of a reflective element that is on a side of a gap or space through which light is to pass through without reflection by the element. In a fan-like assembly, such situations can arise if portions of the fan-like assembly are separated by a gap. Additionally, each part of the fan-like assembly itself features gaps through which light passes. FIG. 13A shows a close-in view of an end of reflective plane 193 at $FP_{18}$. Since the element comprising two-sided reflective plane 193 has a thickness, the front and back sides of reflective plane are shown as $193_{FS}$ and $193_{BS}$. Further, the illustrated portions 193.1, which faces toward FP18, and 193.2, which faces away from FP18, are formed to define an acute angle $\Phi_2$. $\Theta_3$ is also shown for reference only; no particular relationship between $\Phi_2$ and $\Theta_3$ is to be implied. Thus, light rays can pass closer by the edge into the gap (in this example, the space between elements 192 and 193) without interference. When using elements with acute edges, better results can be achieved by selecting the angles of other elements so that reflected rays do not impinge on the backside portions defining the acute angle. In this example, element 192 can be positioned so that rays reflected by the front side of element 192 do not impinge at 193.2, but rather impinge on $193_{BS}$.

Figure 14:
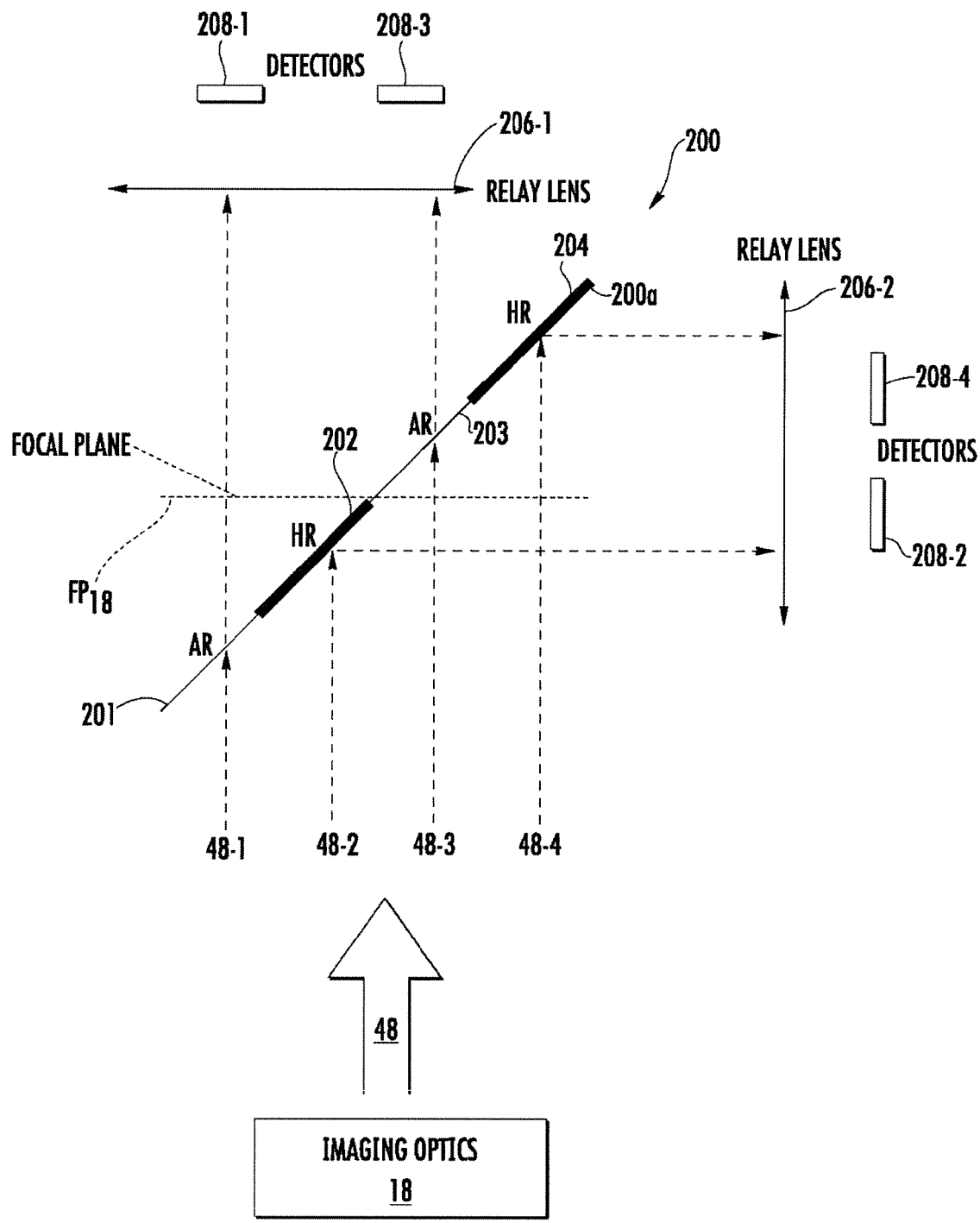
FIG. 14 is a diagram of a splitting apparatus comprising an element with a plurality of transmissive and reflective areas.

FIG. 14 illustrates another embodiment of a splitting apparatus. In this example, splitting apparatus 200 comprises an element 200a having multiple reflective and transmissive areas. In this view, incoming light 48 is comprises four portions 48-1, 48-2, 48-3, and 48-4 which pass through and are redirected by element 200a. Namely, portions 48-1 and 48-3 pass through transmissive portions 201 and 203, while portions 48-2 and 48-4 are reflected by reflective portions 202 and 204. The transmissive and reflective portions are arranged in an alternating pattern in this example. The transmitted portions are imaged onto respective detectors 208-1 and 208-3 by relay lens 206-1, while the reflected portions are imaged onto detectors 208-4 and 208-2 by relay lens 206-2. Although combined relay lenses 206-1 and 206-2 are shown, it will be understood that each portion could utilize its own relay lens.

This splitting apparatus results in a number of areas of non-uniformity equal to the number of split portions minus two. In this example, this will be (4−2)=2 areas of non-uniformity. However, element 200a may be easier to construct and/or place into an inspection tool in some instances. The transmissive portions and reflective portions may be obtained in any suitable manner, such as by using anti-reflection and high-reflection coatings, respectively, on glass or other transmissive material. As another example, the transmissive portions can comprise gaps or holes. In this example, element 200a is positioned at an angle $\Phi$ to $FP_{18}$ of approximately 45 degrees. Other angles may be used in other embodiments.

Although this example is one-dimensional, a two-dimensional element may be constructed, with highly reflective and anti-reflective areas arranged in a checkered pattern. However, a two-dimensional arrangement can result in more non-uniformity. Further, as was discussed above in conjunction with the "W" shaped splitting apparatus, one or more beam sharers may be placed between the detectors in each array. This may result in easier construction or arrangement of detectors and other components.

In any of the embodiments of the present subject matter, the individual relay lenses may be replaced by any suitable optics that contain lenses mirrors, and/or other components. The optics may have any kind of magnification, such as 1:1, enlarging or shrinking. In addition, the angle between the reflecting elements plane may be other than 90 degrees as shown in the figures. It may be 90 degrees, acute or obtuse.

The elements comprising reflective planes may be constructed of any suitable material. For instance, a reflective plane may be obtained using a mirror, a glass or other material treated with a high reflection coating, or may comprise any suitable kind of reflecting component or material. The reflecting elements may reflect essentially 100% of the light or less while the non-reflected light may be transmitted or absorbed. Furthermore, the relative sizes of the mirrors, other reflecting components, relay lenses, and/or the detectors may be different or may be identical. For instance, in some embodiments, an image is split into multiple portions with different sizes from one another which are directed towards detectors of differing sizes. Furthermore, although certain shapes (e.g. "W" shapes and beam splitters) are shown in some examples as comprising multiple elements, such shapes could be formed using single elements with multiple faces corresponding to reflective planes.

In several examples, images were split into a number of portions, with each portion corresponding to a different detector. However, it will be understood that, for a given splitting apparatus, the number of portions may or may not ultimately correspond to the number of detectors. For instance, if a splitting apparatus is cascaded with other splitting apparatus, then the number of detectors will exceed the number of portions created by the first splitting apparatus. Moreover, it will be understood that any embodiment of a splitting apparatus discussed herein can be cascaded any suitable number of times with any other splitting apparatus.

Exemplary detectors were also discussed in several examples above. It will be understood that any suitable type, or combination of types, of detectors can be used, and the particular architecture or principles of operation for detectors can vary. For example, suitable two-dimensional detectors include, but are not limited to, CCD or CMOS detectors.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

The invention claimed is:

1. A semiconductor inspection system configured to create an image of an object at a focal plane, the semiconductor inspection system comprising:

an imaging assembly defining a focal plane;

at least two two-dimensional detectors; and at least one splitting apparatus positioned to split the image of the object at the focal plane into a plurality of portions and direct at least one portion to a two-dimensional detector;

wherein at least one point of the splitting apparatus is placed within the focal plane so that at least some light comprising part of the image of the object reaches the spatial location of the focal plane, the at least one splitting apparatus comprising;

a plurality of reflective planes, the plurality of reflective planes defining an angle between each pair of planes, wherein at least one pair of the planes defines a gap through which at least one portion of the image passes to be focused on a two-dimensional detector, and each remaining portion of the image is directed by a respective reflective plane toward a different two-dimensional detector; and a single optical element comprising a plurality of reflective surfaces that each define a reflective plane and at least one non-reflective surface corresponding to the gap.

2. The semiconductor inspection system set forth in claim 1, wherein an edge of an element defining at least one reflective plane that defines a side of the gap and is closest to the focal plane has an acute angle which allows the portion of the image that passes through the gap to avoid interference from an element comprising the reflective plane.

3. The semiconductor inspection system set forth in claim 1, comprising at least two splitting apparatus, wherein a point of each splitting apparatus is placed in the focal plane.

4. The semiconductor inspection system set forth in claim 1, wherein the intensity and the uniformity of intensity of light comprising each portion at each detector is substantially unafffected by the split.

5. The semiconductor inspection system set forth in claim 4, wherein the image is split to at least three detectors.

6. The semiconductor inspection system set forth in claim 4, wherein the image is split to at least four detectors.

7. The semiconductor inspection system set forth in claim 1, wherein the image intensity and the angular distribution of the light impinging on the two-dimensional detectors is substantially unaffected by the split.

8. The semiconductor inspection system set forth in claim 7, wherein the image is split to at least three detectors.

9. The semiconductor inspection system set forth in claim 7, wherein the image is split to at least four detectors.

10. A semiconductor inspection system configured to create an image of an object at a focal plane, the semiconductor inspection system comprising:

an imaging assembly defining a focal plane;
at least two two-dimensional detectors;
at least one splitting apparatus positioned to split the image of the object at the focal plane into a plurality of portions and direct at least one portion to a two-dimensional detector;
wherein at least one point of the splitting apparatus is placed within the focal plane so that at least some light comprising part of the image of the object reaches the spatial location of the focal plane; and
a reflecting plane, wherein the reflecting plane is curved so as to focus the image at the focal plane to another focal plane or detector.

11. The semiconductor inspection system set forth in claim 10, wherein the intensity and the uniformity of intensity of light comprising each portion at each detector is substantially unafffected by the split.

12. The semiconductor inspection system set forth in claim 11, wherein the image is split to at least three detectors.

13. The semiconductor inspection system set forth in claim 11, wherein the image is split to at least four detectors.

14. The semiconductor inspection system set forth in claim 10, wherein the image intensity and the angular distribution of the light impinging on the two-dimensional detectors is substantially unaffected by the split.

15. The semiconductor inspection system set forth in claim 14, wherein the image is split to at least three detectors.

16. The semiconductor inspection system set forth in claim 14, wherein the image is split to at least four detectors.

* * * * *